(12) United States Patent
Kracker

(10) Patent No.: US 8,086,302 B2
(45) Date of Patent: Dec. 27, 2011

(54) CARDIAC SIGNAL SENSOR CONTROL BASED ON PERFUSION SENSING

(75) Inventor: Stefan G. Kracker, Sonthofen (DE)

(73) Assignee: Medtronic, Inc., Minneapolis, MN (US)

(*) Notice: Subject to any disclaimer, the term of this patent is extended or adjusted under 35 U.S.C. 154(b) by 706 days.

(21) Appl. No.: 12/164,835

(22) Filed: Jun. 30, 2008

(65) Prior Publication Data

US 2009/0326356 A1 Dec. 31, 2009

(51) Int. Cl.
*A61B 5/04* (2006.01)
(52) U.S. Cl. .......................... 600/513; 607/22
(58) Field of Classification Search .......... 600/322–324, 600/508, 509; 607/6, 14, 18, 22, 88
See application file for complete search history.

(56) References Cited

U.S. PATENT DOCUMENTS

| | | | |
|---|---|---|---|
| 4,374,382 A | 2/1983 | Markowitz | |
| 4,903,701 A | 2/1990 | Moore et al. | |
| 4,911,167 A | 3/1990 | Corenman et al. | |
| 4,934,372 A | 6/1990 | Corenman et al. | |
| 5,040,533 A | 8/1991 | Fearnot | |
| 5,365,932 A * | 11/1994 | Greenhut | 600/508 |
| 5,431,170 A | 7/1995 | Mathews | |
| 5,556,421 A | 9/1996 | Prutchi et al. | |
| 5,766,127 A * | 6/1998 | Pologe et al. | 600/310 |
| 5,795,300 A | 8/1998 | Bryars | |
| 6,125,290 A | 9/2000 | Miesel | |
| 6,160,478 A | 12/2000 | Jacobsen et al. | |
| 6,198,952 B1 | 3/2001 | Miesel | |
| 6,331,162 B1 | 12/2001 | Mitchell | |
| 6,491,639 B1 | 12/2002 | Turcott | |
| 6,783,498 B2 | 8/2004 | Sackner et al. | |
| 7,072,702 B2 | 7/2006 | Edgar, Jr. et al. | |
| 7,120,481 B2 | 10/2006 | Keller et al. | |
| 7,142,906 B2 | 11/2006 | Yamashita et al. | |
| 7,286,884 B2 | 10/2007 | Marshall et al. | |
| 7,302,294 B2 | 11/2007 | Kamath et al. | |
| 7,324,848 B1 | 1/2008 | Turcott | |
| 7,376,454 B2 | 5/2008 | Casciani et al. | |
| 2006/0253160 A1 | 11/2006 | Benditt et al. | |
| 2007/0016089 A1 | 1/2007 | Fischell et al. | |
| 2007/0150017 A1 | 6/2007 | Salo | |
| 2007/0156085 A1 | 7/2007 | Schulhauser | |
| 2007/0179366 A1 | 8/2007 | Pwezner et al. | |

(Continued)

OTHER PUBLICATIONS

International Search Report and Written Opinion from PCT Application Serial No. PCT/US2008/009033 mailed Mar. 30, 2009 (13 pages).

(Continued)

*Primary Examiner* — Brian T Gedeon
(74) *Attorney, Agent, or Firm* — Michael C. Soldner

(57) ABSTRACT

An optical perfusion sensor may monitor blood oxygen saturation of blood-perfused tissue, which may be referred to as tissue perfusion, until a tissue perfusion value is within a threshold range of a reference value, and, in some examples, for at least a minimum period of time. The tissue perfusion value may indicate an absolute blood oxygen saturation level or a relative change in blood oxygen saturation level. The reference value may be, for example, determined by an optical oxygenation (O2) variation index that indicates a change in blood oxygen saturation of tissue. In some examples, an operation of a cardiac signal sensing module may be controlled based upon detecting a threshold change in tissue perfusion. For example, the cardiac signal sensing module may be activated upon detecting a threshold change in tissue perfusion.

26 Claims, 12 Drawing Sheets

U.S. PATENT DOCUMENTS

2007/0239053 A1 10/2007 Bhunia
2007/0239215 A1 10/2007 Bhunia
2008/0091242 A1 4/2008 Kamath et al.
2008/0208020 A1* 8/2008 Cinbis et al. .................. 600/323

OTHER PUBLICATIONS

Reply to Written Opinion from PCT Application Serial No. PCT/US2008/009033 filed Aug. 14, 2009 (8 pages).

U.S. Appl. No. 12/181,025, entitled "Implantable Optical Hemodynamic Sensor Including Light Transmission Member", filed Jul. 28, 2008.

U.S. Appl. No. 12/164,491, entitled "Optical Perfusion Sensor Detector", filed Jun. 30, 2008.

U.S. Appl. No. 12/164,776, entitled "Tissue Perfusion Sensor Control", filed Jun. 30, 2008.

U.S. Appl. No. 12/182,847, entitled "Physiological Parameter Monitoring With Minimization of Motion Artifacts", filed Jul. 30, 2008.

* cited by examiner

CARDIAC SIGNAL SENSOR CONTROL BASED ON PERFUSION SENSING

TECHNICAL FIELD

The disclosure relates to medical devices, and, more particularly, to medical devices that monitor one or more physiological parameters of a patient.

BACKGROUND

Some implantable medical devices, such as cardiac monitors, may sense and record cardiac signals of a patient. Example cardiac signals include an electrogram or an electrocardiogram. In some cases, a cardiac monitor may be a part of a device that does not include stimulation capabilities, while in other cases, a cardiac monitor may be incorporated in a device that includes a stimulation generator, which generates and delivers therapy to the patient, such as a pacemaker, cardioverter or defibrillator. Some types of medical devices may only store cardiac signals of interest, such as the signals that exhibit a departure from a normal cardiac signal, e.g., a sinus rhythm.

Cardiac signals recorded by a cardiac monitor may be retrieved and analyzed to diagnose a patient condition, such as syncope or cardiac arrhythmia. For example, a clinician may retrieve the stored cardiac signal data from the implantable device with the aid of an external device that communicates with the implantable device. Syncope and cardiac arrhythmias may be related. For example, syncope may be triggered by a cardiac arrhythmia, such as bradycardia, tachyarrhythmia. However, in some instances, syncope may be unrelated to a cardiac arrhythmia, and may be attributable to, for example, low blood pressure that is not caused by a cardiac arrhythmia.

Syncopic events may occur relatively infrequently and have a relatively short duration and/or a relatively sudden onset. Implantable cardiac monitors may be a useful tool for long-term monitoring of a patient's cardiac signals in order to help diagnose the source of the patient's syncope.

SUMMARY

In general, the disclosure is directed to monitoring blood oxygen saturation levels of tissue with the aid of an implantable medical device (IMD). In some examples, the IMD may include an optical perfusion sensor that includes a light source (e.g., a light emitting diode) that emits light into a blood-perfused tissue site of a patient, and a detector that senses light that was emitted by the light source and transmitted through the blood-perfused tissue or reflected by a blood mass (e.g., a blood vessel).

The detector may generate an electrical signal that indicates an amount (or intensity) of light absorbed and/or reflected by a blood mass within the blood-perfused tissue, from which the blood oxygen saturation level may be determined. Various perfusion values may be derived from the electrical signal generated by the detector of the optical perfusion sensor. A perfusion value may indicate the absolute blood oxygen saturation level or a relative change in the blood oxygen saturation level. Example perfusion values include, but are not limited to, an amplitude of the electrical signal from the detector, an optical oxygenation (O2) variation index, which may indicate a change in blood oxygen saturation level of the tissue, or a relative change in blood pressure.

The IMD may also sense a cardiac signal of a patient, such as an electrogram (EGM) or electrocardiogram (ECG). In some examples described herein, tissue perfusion information is collected following the detection of a cardiac condition, such as a cardiac arrhythmia. In other examples, the optical perfusion sensor is activated at regular time intervals. The optical perfusion sensor may monitor and store perfusion data for a preset period of time or until a perfusion value that is based on the electrical signal generated by the optical perfusion sensor returns to a predetermined range of a reference value.

In some examples, an operation of a cardiac signal sensing module may be modified based on a oxygen saturation level of blood of the patient. For example, the cardiac signal sensing module may be activated upon detecting a threshold change in the blood oxygen saturation level of the patient.

In one aspect, the disclosure is directed to a method comprising receiving an electrical signal from an optical perfusion sensing module, where the electrical signal is indicative of a blood oxygen saturation level of a patient, determining whether a perfusion value based on the electrical signal is within a threshold range of values, and modifying an operation of the optical perfusion sensing module if the perfusion value is within the threshold range of values.

In another aspect, the disclosure is directed to a system comprising an optical perfusion sensing module that generates an electrical signal indicative of a blood oxygen saturation level of a patient, and a processor that receives the electrical signal from the optical perfusion sensing module, determines whether a perfusion value based on the electrical signal is within a threshold range of values, and modifies an operation of the optical perfusion sensing module if the perfusion value is within the threshold range of values.

In another aspect, the disclosure is directed to a system comprising means for receiving an electrical signal from an optical perfusion sensing module, where the electrical signal is indicative of a blood oxygen saturation level of a patient, means for determining whether a perfusion value based on the electrical signal is within a threshold range of values, and means for modifying an operation of the optical perfusion sensing module if the perfusion value is within the threshold range of values.

In another aspect, the disclosure is directed to a computer-readable medium containing instructions. The instructions cause a programmable processor to receive an electrical signal from an optical perfusion sensing module, where the electrical signal is indicative of a blood oxygen saturation level of a patient, determine whether a perfusion value based on the electrical signal is within a threshold range of values, and modify an operation of the optical perfusion sensing module if the perfusion value is within the threshold range of values.

In another aspect, the disclosure is directed to a method comprising receiving an electrical signal from an optical perfusion sensor, where the electrical signal is indicative of blood oxygen saturation of tissue of a patient, and modifying an operation of a cardiac signal sensing module that senses electrical activity of a heart of the patient based on a perfusion value that is based on the electrical signal.

In another aspect, the disclosure is directed to a system comprising an optical perfusion sensing module that generates a first electrical signal indicative of a blood oxygen saturation level of a patient, a cardiac signal sensing module that generates a second electrical signal indicative of electrical activity of a heart of the patient, and a processor that receives the first electrical signal from the optical perfusion sensing module, and modifying an operation of the cardiac signal sensing module based on a perfusion value that is based on the first electrical signal from the optical perfusion sensing module.

In another aspect, the disclosure is directed to a system comprising means for receiving an electrical signal from an optical perfusion sensor, wherein the electrical signal is indicative of blood oxygen saturation of tissue of a patient, and means for modifying an operation of a cardiac signal sensing module that senses electrical activity of a heart of the patient based on a perfusion value that is based on the electrical signal.

In another aspect, the disclosure is directed to a computer-readable medium containing instructions. The instructions cause a programmable processor to receive an electrical signal from an optical perfusion sensor, wherein the electrical signal is indicative of blood oxygen saturation of tissue of a patient, and modify an operation of a cardiac signal sensing module that senses electrical activity of a heart of the patient based on a perfusion value that is based on the electrical signal.

In another aspect, the disclosure is directed to a computer-readable medium containing instructions. The instructions cause a programmable processor to perform a part of the techniques described herein.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Oxygen saturation (or concentration) levels of blood in tissue of a patient may be monitored with the aid of an implantable medical device (IMD) that includes an optical perfusion sensor. In some examples described herein, blood oxygen saturation level information is collected following the detection of a cardiac condition, such as a cardiac arrhythmia. For example, the implantable optical perfusion sensor may be activated upon the detection of the cardiac condition based on the sensed cardiac signal of the patient. In other examples, the optical perfusion sensor is activated at regular time intervals.

Various hemodynamic characteristics may be derived from relative changes in a blood oxygen saturation level of a patient, such as relative changes in the blood pressure of the patient. Therefore, blood oxygen saturation levels may be useful for diagnosing patient conditions, such as the cause of syncope. A syncopic event may be attributable to a drop in blood pressure. As described in further detail below, an implantable medical device that includes an optical perfusion sensor and a cardiac signal sensor may be useful for determining whether a drop in blood pressure occurred before a detected cardiac arrhythmia event, and if so, the duration the blood pressure remained below a threshold level.

In some examples described herein, an operation of a cardiac signal sensing module may be modified (e.g., controlled) based on a oxygen saturation level of blood of the patient. For example, the cardiac signal sensing module may be activated upon detecting a threshold change in the blood oxygen saturation level of the patient. The threshold change may be, for example, a change in the blood oxygen saturation level that indicates a drop in the patient's blood pressure that may reflect an occurrence of a syncopic event. In this way, an IMD may sense and store cardiac signals that correspond to a change in blood oxygen saturation levels of a patient. This may provide a clinician with a useful snapshot of the patient's physiological condition at the time a syncopic event may have occurred.

Figure 1:
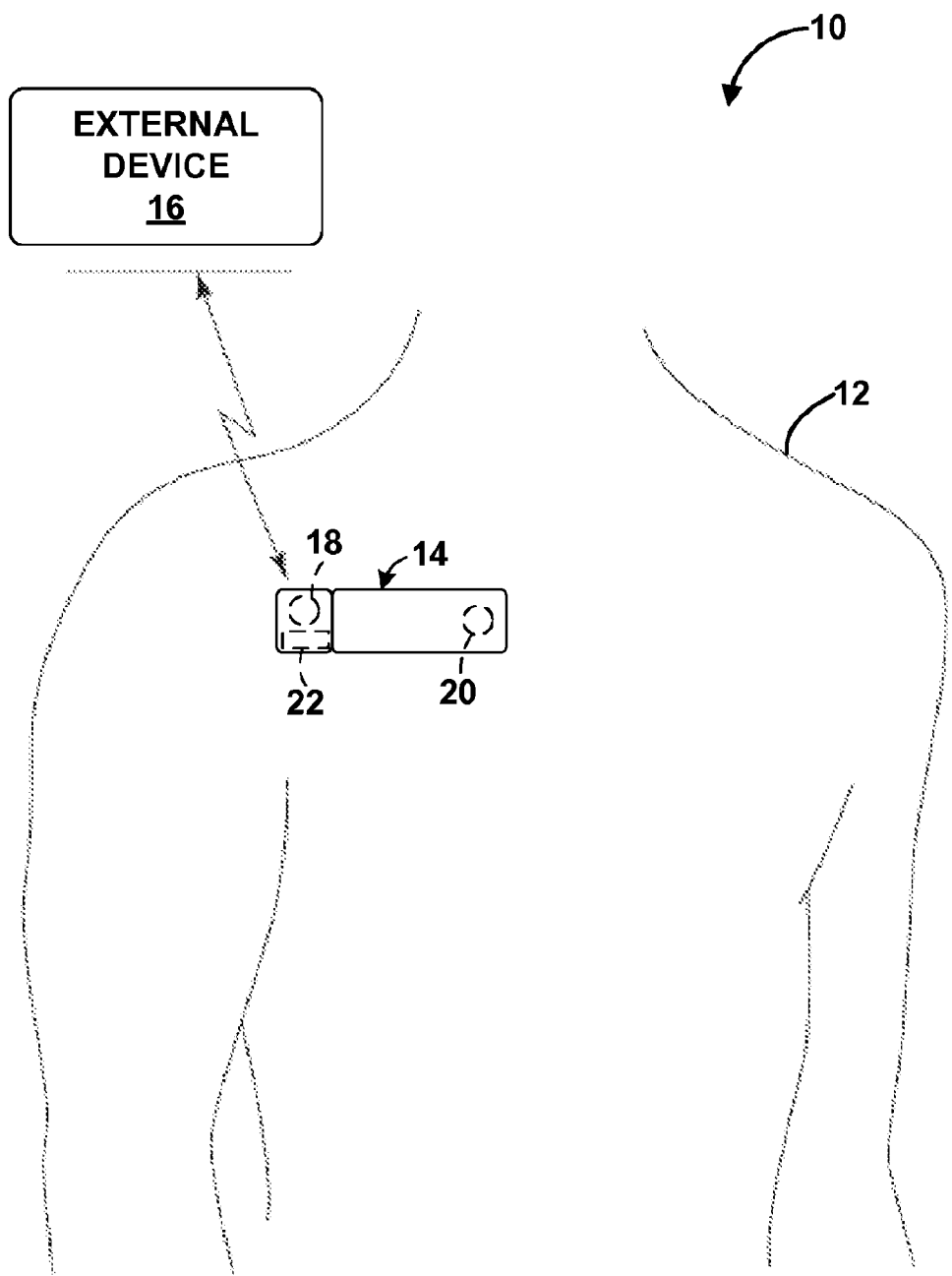
FIG. 1 is a conceptual diagram illustrating an example monitoring system that includes an implantable tissue perfusion sensor.

FIG. 1 is a conceptual diagram illustrating an example monitoring system 10 that may be used to monitor one or more physiological parameters of patient 12, such as cardiac signals of a heart of patient 12 and an oxygen saturation level of blood of patient 12. Patient 12 ordinarily, but not necessarily, will be a human. Monitoring system 10 includes IMD 14 and external device 16. IMD 14 may also be referred to as an implantable monitor. IMD 14 may be, for example, an implantable cardiac monitor that does not provide therapy (e.g., stimulation therapy) to patient 12. In other examples, e.g., as described with respect to FIG. 2, IMD 14 may be incorporated in an implantable medical device that delivers stimulation to the heart of patient 12 or another therapy delivery device (e.g., a neurostimulator). Neither IMD 14 nor external device 16 or any of the figures shown herein are drawn to any particular scale.

In the example shown in FIG. 1, IMD 14 is implanted within a subcutaneous tissue layer of patient 12. Due to its relatively small size, a clinician may implant monitor 14 through a relatively small incision in the patient's skin, or percutaneously, e.g., via an introducer. In other examples, IMD 14 may be implanted within other tissue sites, such as a submuscular location. IMD 14 may be a temporary diagnostic tool employed to monitor one or more physiological parameters of patient 12 for a relatively short period of time (e.g., days or weeks), or may be used on a more permanent basis, such as to control therapy delivery to patient 12. In some examples of the latter use of IMD 14, a separate therapy delivery device, such as a fluid delivery device, pacemaker, cardioverter or defibrillator, may be implanted within patient 12. The therapy delivery device may communicate with IMD 14 via a wired connection or via wireless communication techniques. In other examples, as previously described, IMD 14 may be incorporated in a common housing with a therapy delivery device.

IMD 14 includes electrodes 18, 20 that may sense electrical activity of the heart of patient 12. For example, IMD 14 may generate an electrogram (EGM) or electrocardiogram (ECG) based on signals from electrodes 18, 20. While other types of electrical signals of the heart of patient 12 are contemplated, EGM signals are primarily referred to throughout the remainder of the disclosure. Electrodes 18, 20 may be positioned any suitable distance from each other. In the example shown in FIG. 1, electrodes 18, 20 are coupled to an outer housing of IMD 14. In other examples, electrodes 18, 20 may be coupled to leads that extend from the outer housing of IMD 14.

IMD 14 further includes optical perfusion sensor 22 that generates a signal indicative of the blood oxygen saturation level of blood in a tissue site proximate to optical perfusion sensor 22. Optical perfusion sensor 22 may also be referred to as a "pulse oximeter." The blood oxygen saturation level may be indicative of various hemodynamic characteristics, such as blood pressure of patient 12 or a relative blood flow through the tissue site. An example of optical perfusion sensor 22 is described below with reference to FIG. 3. Although optical perfusion sensor 22 is shown to be on the same surface of IMD 14 as electrodes 18, 20, in other examples, optical perfusion sensor 22 may be on any suitable surface of IMD 14. For example, optical perfusion sensor 22 and at least one of the electrodes 18, 20 may be positioned on different surfaces of the housing of IMD 14 or disposed on a lead or another member that extends from the monitor 14 housing.

IMD 14 may be implanted within patient 12 such that optical perfusion sensor 22 is adjacent to blood-perfused tissue. For example, optical perfusion sensor 22 may be positioned proximate tissue that is near a blood mass (e.g., vasculature, such as one or more blood vessels) of patient 12, but not within a vein, artery, or heart of patient 12. In other examples, optical perfusion sensor 22 may be positioned within a vein or other vasculature of patient 12.

As described in further detail below with reference to FIG. 3, optical perfusion sensor 22 includes at least one light source that emits light at a particular wavelength, which scatters through blood-perfused tissue, and at least one detector that senses the light that is emitted from the light source, and which traversed through blood-perfused tissue and, in some cases, was reflected by a blood mass (e.g., blood in a blood vessel) of patient 12. In some examples, IMD 14 may be implanted within patient 12 such that optical perfusion sensor 22, or at least the light source and detector, face away from the epidermis of patient 12 in order to help minimize interference from background light, e.g., from outside of the patient's body. Background light may include light from a source other than the one or more light sources of optical perfusion sensor 22. Detection of the background light by the detector of optical perfusion sensor 22 may result in an inaccurate and imprecise reading of the level of blood oxygen saturation of the adjacent tissue.

The optical properties of blood-perfused tissue may change depending upon the relative amounts of oxygenated and deoxygenated hemoglobin, due, at least in part, to the different optical absorption spectra of oxygenated and deoxygenated hemoglobin. That is, the oxygen saturation level of the patient's blood may affect the amount of light that is absorbed by a blood mass within the tissue observed by optical perfusion sensor 22 and the amount of light that is reflected by the blood mass. Oxygenated and deoxygenated hemoglobin within the blood may absorb different wavelengths of light. An electrical signal generated by optical perfusion sensor 22 that indicates the intensity of one or more wavelengths of light detected by the detector of sensor 22 may change based on the relative amounts of oxygenated and deoxygenated hemoglobin in the blood mass within the blood-perfused tissue proximate to sensor 22. Accordingly, the intensity of light that is light emitted by the light source of sensor 22 and reflected by blood may indicate relative blood oxygen saturation levels. At least some of the light reflected by the blood may be detected by the detector of optical perfusion sensor 22.

The signal generated by optical perfusion sensor 22 may indicate the relative change in hemoglobin of the blood-perfused tissue that is saturated with oxygen as well as the change in hemoglobin concentration in the tissue. An optical oxygenation (O2) variation index (also referred to as an O2 index) may be calculated based on the intensity of light detected by the one or more detectors of optical perfusion sensor 22. The O2 variation index is typically a unitless number and may indicate a change in blood oxygenation of the tissue adjacent to optical perfusion sensor 22. Example techniques for determining an O2 variation index are described below with reference to FIG. 7. In addition, example techniques for determining an O2 variation index are described in U.S. Patent Application Publication No. 2007/0239053 to Bhunia, entitled, "METHOD AND APPARATUS FOR VERIFYING A DETERMINED CARDIAC EVENT IN A MEDICAL DEVICE BASED ON DETECTED VARIATION IN HEMODYNAMIC STATUS," which was filed on Apr. 28, 2006 and is incorporated herein by reference in its entirety. As described in U.S. Patent Application Publication No. 2007/0239053 to Bhunia et al., a signal based on the O2 variation index may indicate any change in hemodynamic status. A monotonically decreasing trend in the O2 variation index at the onset of a cardiac arrhythmia may confirm the event to be hemodynamically unstable, as in case of ventricular fibrillation.

Changes in blood oxygenation of the tissue adjacent to optical perfusion sensor 22 may indicate various hemodynamic characteristics of patient 12. An example of a hemodynamic characteristic that may be derived from a signal generated by optical perfusion sensor 22 includes arterial blood pressure of patient 12. In some cases, the signal generated by optical perfusion sensor 22 may indicate the blood oxygen saturation level of the tissue. As used herein, "tissue perfusion" may refer to the oxygen concentration of blood in the tissue. The techniques described herein may be used to generally monitor the blood oxygen saturation level of patient 12, which may then be used to monitor the tissue perfusion of a particular tissue region within patient 12. Tissue perfusion and blood oxygenation levels may be interchangeably referred to in the present disclosure.

The presence of cardiac arrhythmias may be derived from a signal generated by optical perfusion sensor 22. As described in U.S. Patent Application Publication No. 2007/0239215 to Bhunia et al., entitled, "METHOD AND APPARATUS FOR USING AN OPTICAL HEMODYNAMIC SENSOR TO IDENTIFY AN UNSTABLE ARRHYTHMIA," which was filed on Mar. 31, 2006 and is incorporated herein by reference in its entirety, electrical signals generated by the detector of optical perfusion sensor 22 may experience a significant change in value following a hemodynamically unstable ventricular fibrillation. In one example provided by U.S. patent application Ser. No. 11/394,477 to Bhunia et al., an optical perfusion sensor includes a red light emitting diode (LED) and an infrared (IR) LED as light sources, and a detector. An increase in a red optical signal sensed by the detector, which may indicate the amount of red light from the red LED that was reflected by blood in the tissue proximate to optical perfusion sensor 22, and a decrease in an IR signal sensed by the detector, which may indicate the amount of IR light form the IR LED that was reflected by blood in the tissue in blood-perfused tissue, may indicate the occurrence of a cardiac arrhythmia.

Optical perfusion sensor 22 may include a programmable detection window and a programmable detection threshold. A detection window may indicate the duration of time during which optical perfusion sensor 22 actively monitors blood oxygen saturation levels of blood of patient 12. In some examples, the detection window for optical perfusion sensor 22 may be programmed as a minimum period of time (measured continuously) during which optical perfusion sensor 22 actively senses tissue perfusion. The minimum period of time may also be minimum duration of time for which IMD 14 stores the signal generated by optical perfusion sensor. Thus, the minimum period of time may define the size of each set of tissue perfusion information stored by IMD 14.

A detection threshold value may be a change in an O2 variation index that is considered to indicate an acceptable change in oxygen saturation levels, e.g., a range of values that do not indicate the presence of a cardiac arrhythmia or syncope. The detection threshold value may, for example, indicate a percentage change in the O2 variation index, an absolute change in the O2 variation index, different values for positive and negative changes (e.g., indicating relative increase and decreases, respectively, in the blood oxygen saturation level). Example techniques for determining an O2 variation index are described below with reference to FIG. 7.

If the O2 variation index changes by more than the detection threshold value, IMD 14 may generate an event indication. Because the O2 variation index may indicate the oxygenation of blood of the tissue proximate to optical perfusion sensor 22, which may be related to blood pressure of patient 12, the event indication may indicate, for example, that a syncope was detected or a cardiac arrhythmia was detected. Example detection threshold values for detecting a ventricular fibrillation or syncope based on a change in an O2 variation index include, for example, 0.005-0.015.

The detection window duration and detection threshold value may affect the specificity and sensitivity of optical perfusion sensor 22 in detecting a patient event that is associated with a change in blood oxygenation, such as a cardiac arrhythmia event or syncopic event. Sensitivity of optical perfusion sensor 22 may refer to the ability of sensor 22 to detect the patient event. Decreasing the sensitivity level of sensor 22 may adversely affect the ability of optical perfusion sensor 22 to detect the patient event. Specificity may refer to the ability of sensor 22 to properly detect the change in the blood oxygenation, e.g., to correctly identify that the O2 variation index changed by the detection threshold value. As specificity decreases, optical perfusion sensor 22 may detect fewer changes in blood oxygenation that indicates the occurrence of the patient event. The specificity of optical perfusion sensor 22 may affect the accuracy with which optical perfusion sensor 22 generates an event indication.

In some cases, for a given detection window duration, the specificity of optical sensor 22 may improve by decreasing a detection threshold value. However, at times, the sensitivity may also decrease as a result of decreasing the detection threshold. In addition, in some cases, for a given detection threshold value, increasing a detection window duration may increase the sensitivity of optical perfusion sensor 22 to changes in tissue perfusion, but, at times, the specificity may also decrease by increasing the detection window duration. A clinician or another user may program optical perfusion sensor 22 with a detection threshold and detection window duration that provides a desirable sensitivity and specificity. For example, in some cases, if IMD 14 is used to monitor tissue perfusion of patient 12 to diagnose a cause of syncope, it may be desirable to operate with a high specificity, such as about 90% to about 100% specificity, even if it results in a loss of sensitivity. In some examples, the detection window duration may be about 8 seconds to about 10 seconds and the detection threshold value may be about 0.01.

IMD 14 may store detection information that associates the detection threshold value with a particular patient condition. That is, the detection threshold value may indicate the relative change in blood oxygen saturation level that indicates the occurrence of a particular patient condition. IMD 14 may then generate and store a patient condition indication upon detecting a particular change in the blood oxygenation level that corresponds to the detection threshold value. Alternatively, IMD 14 may merely record the signal from optical perfusion sensor 22 for later analysis by a clinician. The clinician may determine whether any patient events occurred based on the recorded signals from optical perfusion sensor 22, and, in some cases, recorded cardiac signals.

In some examples, the detection window duration and the detection threshold value may be programmable. Different patients may exhibit different tissue perfusion activity, and, therefore, the detection window for detecting a change in tissue perfusion that is indicative of a particular patient event may differ based on the particular patient. In addition, the detection threshold value may affect the sensitivity and specificity of optical sensor 22 in different ways for different patients. By enabling a clinician to select the detection window duration and the detection threshold value, a clinician may personalize the specificity and sensitivity of optical sensor 22 to the particular patient.

As described in further detail below with reference to FIG. 4, IMD 14 may include a memory that stores EGM signals and tissue perfusion information (e.g., electrical signals generated by optical perfusion sensor 22 or data derived from the electrical signal). In some examples, IMD 14 may store the tissue perfusion information that corresponds in time to the sensed EGM signals (or other cardiac signals), such that a clinician may determine what the patient's cardiac activity indicated at the time a particular blood oxygen saturation level was observed.

IMD 14 may be useful for monitoring physiological parameters, such as the EGM and blood pressure, of patient 12. The monitored physiological parameter values may provide useful information for diagnosing a patient condition or formulating a treatment plan for patient 12. For example, if patient 12 experiences syncope, e.g., periodic fainting, IMD 14 may be used to determine the physiological parameters that are associated with the syncopic events. A clinician may review the associated physiological parameters to determine a potential cause of the syncope.

Syncope may be triggered by a cardiac arrhythmia, such as a bradycardia event or episode, which includes more than one event. A bradycardia event may be determined, e.g., based on a duration of a cardiac cycle. A cardiac cycle duration may be, for example, measured between successive R-waves or P-waves of the EGM signal. This duration may also be referred to as an R-R or P-P interval.

The concentration of oxygen in blood in tissue of patient 12 may change in response to a change in a cardiac arrhythmia event or episode. However, in some cases, there may be a delay between the start of the cardiac arrhythmia event and the change in the tissue perfusion, e.g., a change in the blood oxygen saturation level. For example, a cardiac signal (e.g., an ECG or EGM signal) may indicate a cardiac arrhythmia event or episode before the tissue perfusion change is detected. This delay between the detection of a cardiac event and an observed change of tissue perfusion may be useful for diagnosing the cause of a patient's syncope.

In some cases, a clinician may review tissue perfusion information and cardiac signal information stored in IMD 14 to determine whether a change in tissue perfusion of tissue occurred after a cardiac arrhythmia event or before the cardiac arrhythmia event. If the change in tissue perfusion occurred after the cardiac arrhythmia event was detected, the clinician may determine that the physiological parameter values of patient 12 suggest that a syncopic event that occurred substantially at the same time as the cardiac arrhythmia may be at least partially attributable to the cardiac arrhythmia. On the other hand, if the change in tissue perfusion occurred before the cardiac arrhythmia event was detected, the clinician may determine that the physiological parameter values of patient 12 suggest that a syncopic event was attributable to a patient condition other than the cardiac arrhythmia. For example, a syncopic event may be attributable to a neurocardiogenic syndrome, which may be a dysregulation of the peripheral and/or central autonomous nervous system. Neurocardiogenic syncope may also be referred to as or neurogenic syncope, vasovagal syncope or neutrally mediated syncope. In patients with neurocardiogenic syndrome, blood vessels may expand, which may result in a decrease in blood volume that reaches the patient's brain, which may cause a syncope event. In some cases, neurocardiogenic syncope events may occur due to emotionally stressful events or physical exercise, although other triggering circumstances are also possible.

The date and time of the actual occurrence of the patient's syncopic events may be tracked using any suitable technique. For example, patient 12 may carry external device 16 and input information indicating the date and approximate time of the occurrence of a syncopic event, and, in some cases, the duration of the syncopic event. In other examples, a clinician may associate a detected cardiac arrhythmia event with a syncopic event without confirmation that the syncopic event actually occurred.

In some examples described herein, optical perfusion sensor 22 is configured to periodically monitor the blood oxygen saturation level of adjacent tissue. Compared to continuous monitoring of the blood oxygen saturation level, periodic monitoring may help minimize power consumption by optical perfusion sensor 22, thereby conserving battery resources to promote device longevity. IMD 14 may include a processor that controls optical perfusion sensor 22, such as when optical perfusion sensor 22 actively monitors tissue perfusion. In some examples, IMD 14 may include a processor that controls optical perfusion sensor 22 based on cardiac activity of patient 12, which may be sensed based on an EGM or ECG signal generated with electrodes 18, 20. In one example of controlling the operation of optical perfusion sensor 22, the processor within IMD 14 may collect tissue perfusion information from optical perfusion sensor 22 upon detecting a cardiac arrhythmia event, such as a bradycardia event, ventricular tachycardia event or ventricular fibrillation event, or a cardiac arrhythmia episode (comprising more than one event). This technique for controlling the active tissue perfusion monitoring by optical perfusion sensor 22 may help reduce the power consumed by optical perfusion sensor 22, while still obtaining relevant tissue perfusion information.

Collecting and storing tissue perfusion information upon detecting a cardiac arrhythmia event or episode may be useful for determining the relationship between a change in tissue perfusion (or blood oxygen saturation level) and a cardiac event. For example, as described above, the clinician may review the stored information to determine whether the change in blood oxygen saturation level of the tissue occurred before or after the cardiac arrhythmia event was detected. If the tissue perfusion information indicates the tissue perfusion was relatively low, e.g., deviating from a reference value by a predetermined amount, the stored information may indicate that the change in the blood oxygen saturation level occurred before the cardiac arrhythmia was detected.

In some examples, the clinician may detect a change in tissue perfusion based on a perfusion value that is derived from the electrical signal generated by the detector of optical perfusion sensor 22. For example, the perfusion value may be an amplitude of the electrical signal. In some examples, the clinician may determine whether the tissue perfusion (or oxygen saturation level) was at an acceptable level by comparing the amplitude of the signal from the detector of sensor 22 to a stored reference value that indicates the average amplitude value for a predetermined period of time. As another example, the perfusion value may include an O2 variation index. The clinician may compare the deviation of an O2 variation index value from values indicated by a trend in the O2 variation index over a sample period of time, as described with reference to FIGS. 7 and 8, to determine whether the tissue perfusion was at an acceptable level.

In other examples, optical perfusion sensor 22 may actively monitor tissue perfusion according to a predetermined schedule. For example, IMD 14 may be programmed such that optical perfusion sensor 22 monitors tissue perfusion for a minimum detection window at intervals of about one minute to every 60 minutes. Other time intervals are contemplated.

Some power may be provided to optical perfusion sensor 22 when optical perfusion sensor 22 is not actively monitoring tissue perfusion. Thus, reference to "activating" optical perfusion sensor 22 in response to certain events or in accordance with a schedule may refer to the active storing of signals from optical perfusion sensor 22 within a memory of IMD 14, rather than the powering on and off of optical perfusion sensor 22. However, in some examples, optical perfusion sensor 22 may be powered on when active tissue perfusion monitoring is activated, and then powered off following a predetermined duration of time or upon the return of the blood oxygen saturation level of the patient to a particular value. When optical perfusion sensor 22 is not activated, e.g., when the perfusion sensing triggers have not occurred, IMD 14 may not actively record signals from optical perfusion sensor 22.

As described in further detail below, in some examples, the duration during which optical perfusion sensor 22 actively senses the blood oxygen concentration of blood in the adjacent tissue, i.e., a tissue perfusion sensing time window, may be determined based on the hemodynamic activity of patient 12. In some examples, optical perfusion sensor 22 may sense blood oxygen saturation levels until a perfusion value based on the electrical signal generated by the detector of optical perfusion sensor 22 is within a predetermined range of a reference value, which may be determined by IMD 14 or may be predetermined by a clinician or another user, or otherwise selected. The reference value may include, for example, an average value of a characteristic of the electrical signal generated by optical perfusion sensor 22. The characteristic of the electrical signal may be, for example, an amplitude or a rate of change of the electrical signal over time. In some examples, optical perfusion sensor 22 may periodically collect tissue perfusion information, e.g., every few minutes to every hour or more, in order to generate the reference value. Thus, the average tissue perfusion value may be a running average for a predetermined time period preceding the current time. An example technique for generating a reference value is described with reference to FIG. 11.

In other examples, the reference value may include an O2 variation index value that corresponds to an O2 variation index trend. As previously indicated, the electrical signal may indicate the intensity of light that is detected by the detector of optical perfusion sensor 22. As described below with reference to FIGS. 7 and 8, the O2 variation index value may be derived from the intensity of light detected by the detector.

By sensing and recording tissue perfusion information during a time period in which the perfusion value may indicate a change in the patient's physiological condition, e.g., when the perfusion value differs from a reference value, relevant tissue perfusion data may be stored for later analysis by a clinician. In addition to the tissue perfusion values, the stored tissue perfusion data may indicate the amount of time it took for the patient's blood oxygen saturation level to return to a normal range of values. This time may also indicate the time it took for the patient's blood pressure to return to a normal range of values. A normal range of values may be, for example, determined by the clinician or may be determined based on a signal generated by optical perfusion sensor 22. In some examples, the normal range of values may be represented by an O2 variation index trend that is determined during a sample collection period may indicate a normal range of values.

The associated EGM signals may also be stored with the tissue perfusion information within a memory of IMD 14. If patient 12 experiences periodic syncopic events, the stored tissue perfusion information and EGM signals may be useful for analyzing the patient's physiological state (e.g., blood pressure) at the time a syncopic event, which may be used to diagnose the cause of the syncope.

In some examples, a clinician may retrieve stored EGM and tissue perfusion information from IMD 14 after explanting monitor 14 from patient 12. In other examples, the clinician (or other user) may interrogate monitor 14 with external device 16 while monitor 14 remains implanted within patient 12 in order to retrieve stored information from IMD 14.

External device 16 may be a handheld computing device or a computer workstation. External device 16 may include a user interface that receives input from a user, such as a clinician. The user interface may include, for example, a keypad and a display, which may for example, be a cathode ray tube (CRT) display, a liquid crystal display (LCD) or LED display. The keypad may take the form of an alphanumeric keypad or a reduced set of keys associated with particular functions. External device 16 can additionally or alternatively include a peripheral pointing device, such as a mouse, via which a user may interact with the user interface. In some embodiments, a display of external device 16 may include a touch screen display, and a user may interact with external device 16 via the display.

A user, such as a physician, technician, or other clinician, may interact with external device 16 to communicate with IMD 14. For example, the user may interact with external device 16 to retrieve physiological or diagnostic information from IMD 14. A user may also interact with external device 16 to program implantable monitor, e.g., select values for operational parameters of monitor 14.

For example, the user may use external device 16 to retrieve information from IMD 14 regarding the rhythm of the heart of patient 12 (e.g., determined based on an EGM signal), trends of the heart rhythm over time, or arrhythmia episodes. As another example, the user may use external device 16 to retrieve information from IMD 14 regarding other sensed physiological parameters of patient 12, such as tissue perfusion data, activity, posture, respiration, or thoracic impedance. As another example, the user may use external device 16 to retrieve information from IMD 14 regarding the performance or integrity of IMD 14.

IMD 14 and external device 16 may communicate via wireless communication using any techniques known in the art. Examples of communication techniques may include, for example, low frequency or radiofrequency (RF) telemetry, but other techniques are also contemplated. In some examples, external device 16 may include a programming head that may be placed proximate to the patient's body near the implant site of the IMD 14 in order to improve the quality or security of communication between IMD 14 and external device 16.

Figure 2:
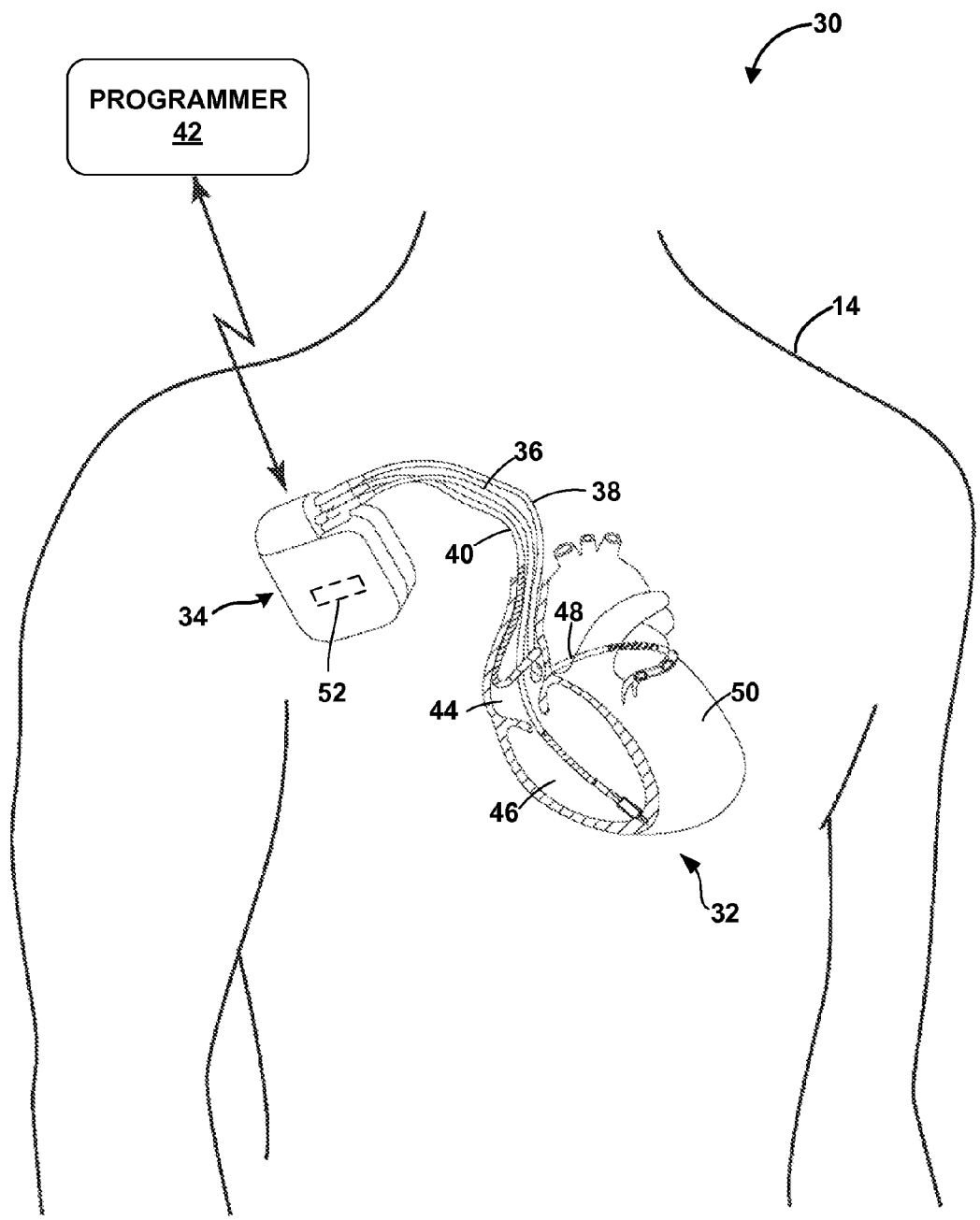
FIG. 2 is a conceptual diagram illustrating an example therapy system that includes an implantable medical device with a tissue perfusion sensor

FIG. 2 is a conceptual diagram illustrating an example therapy system 30 that may be used to provide therapy to heart 32 of patient 12. Therapy system 30 includes IMD 34, which is coupled to leads 36, 38, and 40, and programmer 42. IMD 34 may be, for example, an implantable pacemaker, cardioverter, and/or defibrillator that provides electrical signals to heart 32 via electrodes coupled to one or more of leads 36, 38, and 40.

Leads 36, 38, 40 extend into the heart 32 of patient 12 to sense electrical activity of heart 32 and/or deliver electrical stimulation to heart 32. In the example shown in FIG. 2, right ventricular (RV) lead 36 extends through one or more veins (not shown), the superior vena cava (not shown), and right atrium 44, and into right ventricle 46. Left ventricular (LV) coronary sinus lead 38 extends through one or more veins, the vena cava, right atrium 44, and into the coronary sinus 48 to a region adjacent to the free wall of left ventricle 50 of heart 32. Right atrial (RA) lead 40 extends through one or more veins and the vena cava, and into the right atrium 44 of heart 32.

IMD 34 may sense electrical signals attendant to the depolarization and repolarization of heart 32 via electrodes (not shown in FIG. 2) coupled to at least one of the leads 36, 38, 40. In some examples, IMD 34 provides pacing pulses to heart 32 based on the electrical signals sensed within heart 32. The configurations of electrodes used by IMD 34 for sensing and pacing may be unipolar or bipolar. IMD 34 may also provide defibrillation therapy and/or cardioversion therapy via electrodes located on at least one of the leads 36, 38, 40. IMD 34 may detect arrhythmia of heart 32, such as fibrillation of ventricles 46, 50, and deliver defibrillation therapy to heart 32 in the form of electrical pulses. In some examples, IMD 34 may be programmed to deliver a progression of therapies, e.g., pulses with increasing energy levels, until a fibrillation of heart 32 is stopped. IMD 34 detects fibrillation employing one or more fibrillation detection techniques known in the art.

IMD 34 includes optical perfusion sensor 52, which is similar to optical perfusion sensor 22 described above with respect to FIG. 1. IMD 34 may include features similar to those described with respect to IMD 14. Accordingly, the techniques for controlling tissue perfusion monitoring of optical perfusion sensor 22 (FIG. 1) described herein are also applicable to the control of optical perfusion sensor 52 by a processor/controller within IMD 34.

In some examples, programmer 42 may be similar to external device 16 of monitoring system 10 (FIG. 1). In addition, a user may use programmer 42 to program a therapy progression, select electrodes used to deliver defibrillation pulses, select waveforms for the defibrillation pulse, or select or configure a fibrillation detection algorithm for IMD 34. The user may also use programmer 42 to program aspects of other therapies provided by IMD 34, such as cardioversion or pacing therapies. In some examples, the user may activate certain features of IMD 34 by entering a single command via programmer 42, such as depression of a single key or combination of keys of a keypad or a single point-and-select action with a pointing device.

IMD 34 and programmer 42 may communicate via wireless communication using any techniques known in the art. Examples of communication techniques may include, for example, low frequency or RF telemetry, but other techniques are also contemplated. In some examples, programmer 42 may include a programming head that may be placed proximate to the patient's body near the IMD 34 implant site in order to improve the quality or security of communication between IMD 34 and programmer 42.

Figure 3:
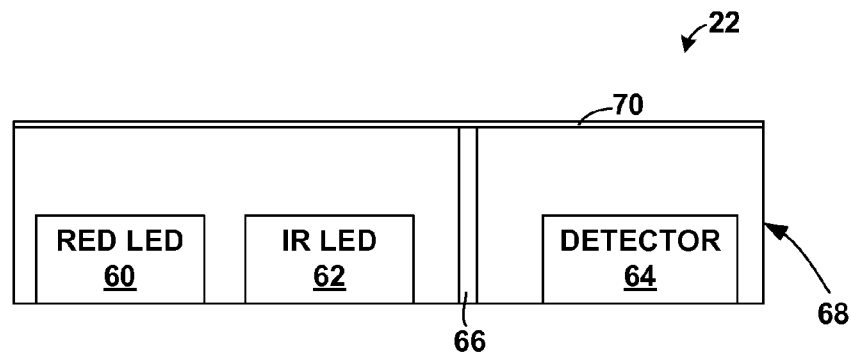
FIG. 3 is a conceptual illustration of an implantable medical device (IMD) that includes an implantable optical tissue perfusion sensor.

FIG. 3 is a conceptual illustration of an example optical perfusion sensor 22 of IMD 14. In the example shown in FIG. 3, optical perfusion sensor 22 includes red LED 60, IR LED 62, detector 64, and optical barrier 66. Red LED 60 may emit light in the red portion of the visible light spectrum, such, but not limited to, light having a wavelength in a range of about 550 nanometers (nm) to about 750 nm. IR LED 62 may emit IR light in the IR portion of the light spectrum, such as, but not limited to, light having a wavelength in a range of about 750 nm to about 2.5 micrometers or greater. Detector 64 is configured to detect light emitted from red LED 60 and IR LED 62, and may include, for example, a photodetector, such as a photodiode. Detector 64 may convert sensed light into either a current or voltage, which may be outputted as an electrical signal. An intensity of the signal received by detector 64 may be indicative of hemodynamic function, such as oxygen saturation of blood or the blood pressure of patient 12. In examples in which detector 64 includes a photodiode, an electrical signal outputted by detector 64 may be directly or inversely proportional to the amount of light (e.g., the intensity of light) incident on the photodiode.

Red LED 60, IR LED 62, detector 64, and optical barrier 66 may be positioned within sensor housing 68. In some examples, sensor housing 68 is defined by a recess within an outer housing of IMD 14, and red LED 60, IR LED 62, detector 64 may be disposed within the recess. In other examples, sensor housing 68 may at least partially extend from an outer housing of IMD 14, such that at least a part of optical perfusion sensor 22 protrudes from the outer housing of IMD 14.

In some examples, optical perfusion sensor 22 may include lens 70 that helps focus light emitted from red LED 60 and IR LED 62. Red LED 60 and IR LED 62 are configured to emit light through lens 70, and detector 64 is configured to detect light received through lens 70. Optical barrier 66 may be positioned within optical perfusion sensor housing 68 to block direct transmission of light from LEDs 60, 62 to detector 64.

Optical perfusion sensor 22 may be subcutaneously implanted within patient 12 such that lens 70 is oriented toward blood perfused tissue of patient 12, e.g., proximate to vasculature of patient 12. In the example of FIG. 3, red LED 60 and IR LED 62 are positioned on the same side of the blood perfused tissue as detector 64, such that detector 64 detects light emitted from LEDs 60, 62 and reflected by the patient's blood. For example, red LED 60, IR LED 62, and detector 64 may be coupled to a common surface of the IMD 14 housing. This type of optical perfusion sensor may be referred to as a reflective perfusion sensor. In other examples, LEDs 60, 62 may be positioned on an opposite side of the blood perfused tissue from detector 64, such that detector 64 detects light that is transmitted through the blood perfused tissue. This latter example is commonly referred to as a transmissive perfusion sensor.

In other examples, optical perfusion sensor 22 may include any two or more light sources for producing at least two different wavelengths of light. The light sources and detector 60 may have any suitable arrangement.

Figure 4:
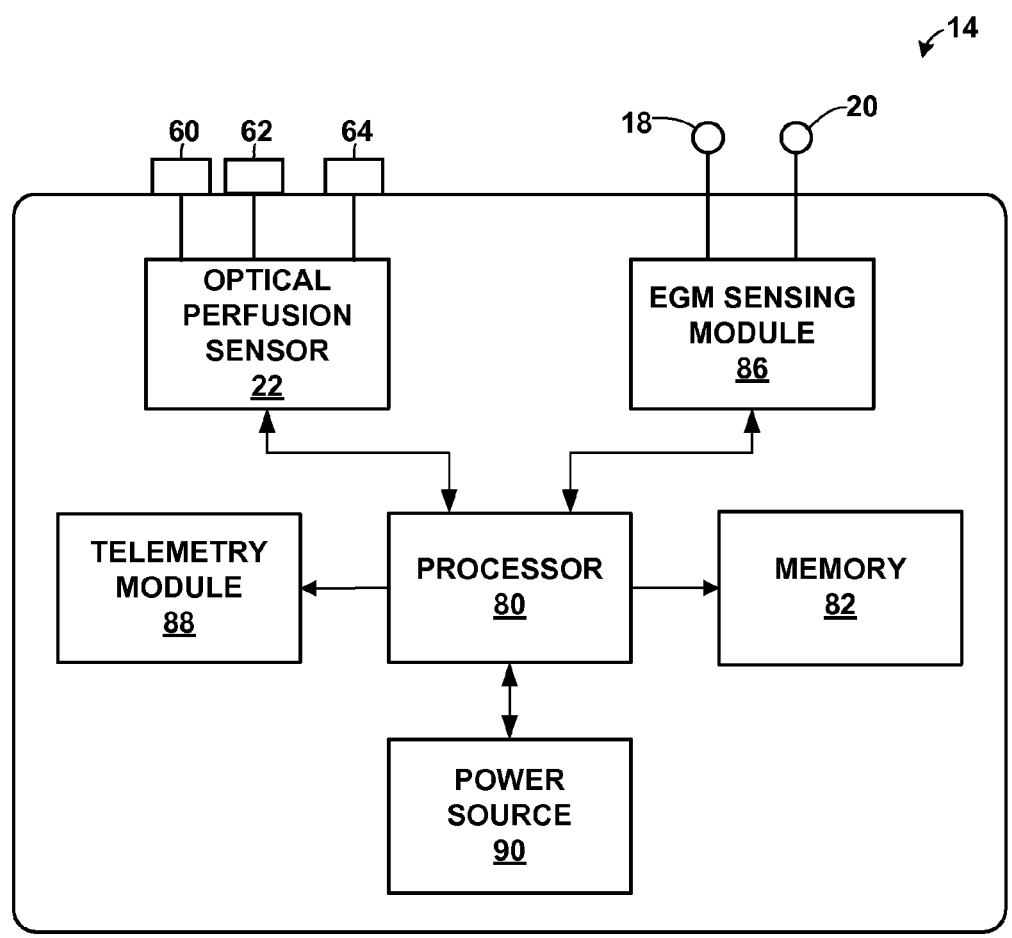
FIG. 4 is a functional block diagram of an example IMD that includes an optical tissue perfusion sensor.

FIG. 4 is a block diagram of an example IMD 14. In the example shown in FIG. 4, IMD 14 includes optical perfusion sensor 22, processor 80, memory 82, EGM sensing module 86, telemetry module 88, and power source 90. Memory 82 includes computer-readable instructions that, when executed by processor 80, cause IMD 14 and processor 80 to perform various functions attributed to IMD 14 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more microprocessors, controllers, digital signal processors (DSPs), application specific integrated circuits (ASICs), field-programmable gate arrays (FPGAs), or equivalent discrete or integrated logic circuitry, or combinations thereof. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls EGM sensing module 86 to sense EGM signals of heart 32 of patient 12 (FIG. 2) and stores EGM signals from EGM sensing module 86 in memory 82.

Processor 80 controls optical perfusion sensor 22 to sense the blood oxygen concentration of tissue adjacent to red LED 60, IR LED 62, and detector 64. Processor 80 may store electrical signals generated by detector 64 of optical perfusion sensor 22 or perfusion values derived from the electrical signals generated by detector 64 in memory 82. Processor 80 may control the operation of red LED 60 and IR LED 62. In some examples, processor 80 may control red LED 60 and IR LED 62 to sequentially emit light, such that only one of the LEDs 60, 62 emits light at a time.

Processor 80 may also control the operation of detector 64. Light sensed by detector 64 may include information about the intensity of red light emitted by red LED 60 and transmitted through blood perfused tissue, as well as the intensity of IR light emitted by IR LED 62 and transmitted through the blood perfused tissue. In order to separate the signals indicative of the red light and IR light, processor 80 may demodulate the electrical signal received from detector 64.

EGM sensing module 86 is electrically coupled to electrodes 18, 20. Electrodes 18, may be coupled to a surface of an outer housing of IMD 14 or may be coupled to a housing of IMD 14, e.g., with the aid of one or more medical leads that extend from the housing. In some examples in which electrodes 18, 20 are coupled to a surface of the outer housing of IMD 14, electrodes 18, 20 may be formed by the housing (e.g., by exposed portions of an electrically conductive housing) or may be attached to the outer surface of the housing.

EGM sensing module 86 monitors signals from at least one of electrodes 18, 20 in order to monitor electrical activity of heart 32, e.g., via EGM signals or ECG signals. In other examples, EGM sensing module 86 may be electrically coupled to more than two electrodes. In some examples, EGM sensing module 86 may include a channel that comprises an amplifier with a relatively wide-band. Signals from sensing electrodes 18, 20 may be coupled to the wide-band amplifier and provided to a multiplexer. Thereafter, the signals may be converted to multi-bit digital signals by an analog-to-digital converter for storage in memory 82 as an EGM. In some examples, the storage of such EGMs in memory 82 may be under the control of a direct memory access circuit.

In some examples, processor 80 may employ digital signal analysis techniques to characterize the digitized signals stored in memory 82 to detect and classify the patient's heart rhythm from the electrical signals. Processor 80 may detect and classify the heart rhythm of patient 12 by employing any of the numerous signal processing methodologies known in the art. In other examples, processor 80 may not analyze the stored EGM signals, and such processing may be done by another processor, such as a processor within external device 16 (FIG. 1), programmer 42 (FIG. 2) or another external computing device.

Processor 80 may generate and store marker codes in some examples. The marker codes may be indicative of different cardiac episodes that EGM sensing module 86 detects, and store the marker codes in memory 82 and/or transmit the marker codes to external device 16 or another external computing device. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

Telemetry module 88 includes any suitable hardware, firmware, software or any combination thereof for communicating with another device, such as external device 16 (FIG. 1) or programmer 42 (FIG. 2). Under the control of processor 80, telemetry module 88 may receive downlink telemetry from and send uplink telemetry to external device 16 or programmer 42 with the aid of an antenna, which may be internal and/or external. Processor 80 may provide the data to be uplinked to external device 16 and the control signals for the telemetry circuit within telemetry module 88, e.g., via an address/data bus. In some examples, telemetry module 88 may provide received data to processor 80 via a multiplexer.

The various components of IMD 14 are coupled to power source 90, which may include a rechargeable or non-rechargeable battery. A non-rechargeable battery may be selected to last for several years, while a rechargeable battery may be inductively charged from an external device, e.g., on a daily or weekly basis.

The block diagram shown in FIG. 4 is merely one example of an IMD 14. In other examples, IMD 14 may include fewer or more components. For example, in examples in which IMD 14 is incorporated with a medical device that delivers therapy to patient 12, IMD 14 may also include a therapy delivery module, such as an electrical stimulation generator or a fluid pump. For example, IMD 14 may include a therapy delivery module that delivers pacing, defibrillation or cardioversion pulses to heart 32 (FIG. 2) of patient 12, or may generate and deliver neurostimulation signals to a target tissue site within patient 12 (e.g., proximate to a spine or nerve, or to a target region of tissue that may or may not be near a nerve).

Although optical perfusion sensor 22 and EGM sensing module 86 are shown to be separate from processor 80 in FIG. 4, in other examples, processor 80 may include the functionality attributed to optical perfusion sensor 22 and/or EGM sensing module 86 herein. For example, optical perfusion sensor 22 and EGM sensing module 86 shown in FIG. 4 may include software executed by processor 80. If optical perfusion sensor 22 or EGM sensing module 84 includes firmware or hardware, optical perfusion sensor 22 or EGM sensing module, respectively, may be a separate one of the one or more processors 80 or may be a part of a multifunction processor. As previously described, processor 80 may comprise one or more processors.

In some examples, some of the components of IMD 14 shown in the example of FIG. 4 may be relocated in another device. For example, optical perfusion sensor 22 may be separate from IMD 14. That is, although optical perfusion sensor 22 is shown in FIG. 4 to be incorporated within a housing of IMD 14 that also encloses other components, such as processor 80 and EGM sensing module 86, in other examples, optical perfusion sensor 22 may be enclosed in a separate housing as part of a separate optical perfusion sensor 22. The optical perfusion sensor 22 that is enclosed in a separate housing from the IMD 14 housing may be mechanically coupled to IMD 14 or may be mechanically decoupled from IMD 14. For example, in some examples, optical perfusion sensor 22 including red LED 60, IR LED 62, detector 64, optical barrier 66, and lens 70 may be implanted within patient 12 at a separate location from IMD 14. Optical perfusion sensor 22 may communicate with IMD 14 via a wired connection or via wireless communication techniques, such as RF telemetry.

In yet other examples, at least a part of optical perfusion sensor 22 may be external to patient 12. For example, optical perfusion sensor 22 may monitor the blood oxygen saturation level of tissue of patient 12 through an epidermis of patient (e.g., through skin on a finger, earlobe or forehead of patient 12). Optical perfusion sensor 22 may transmit the electrical signals generated by detector 64 that are indicative of the sensed intensity of red light and IR light to another device, such as IMD 14, external device 16 or programmer 42. In some examples, data from at least one of optical perfusion sensor 22 or EGM sensing module 86 may be uploaded to a remote server, from which a clinician or another user may access the data to analyze the patient's condition. An example of a remote server is a server provided via the Medtronic CareLink® Network, available from Medtronic, Inc. of Minneapolis, Minn.

Figure 5:
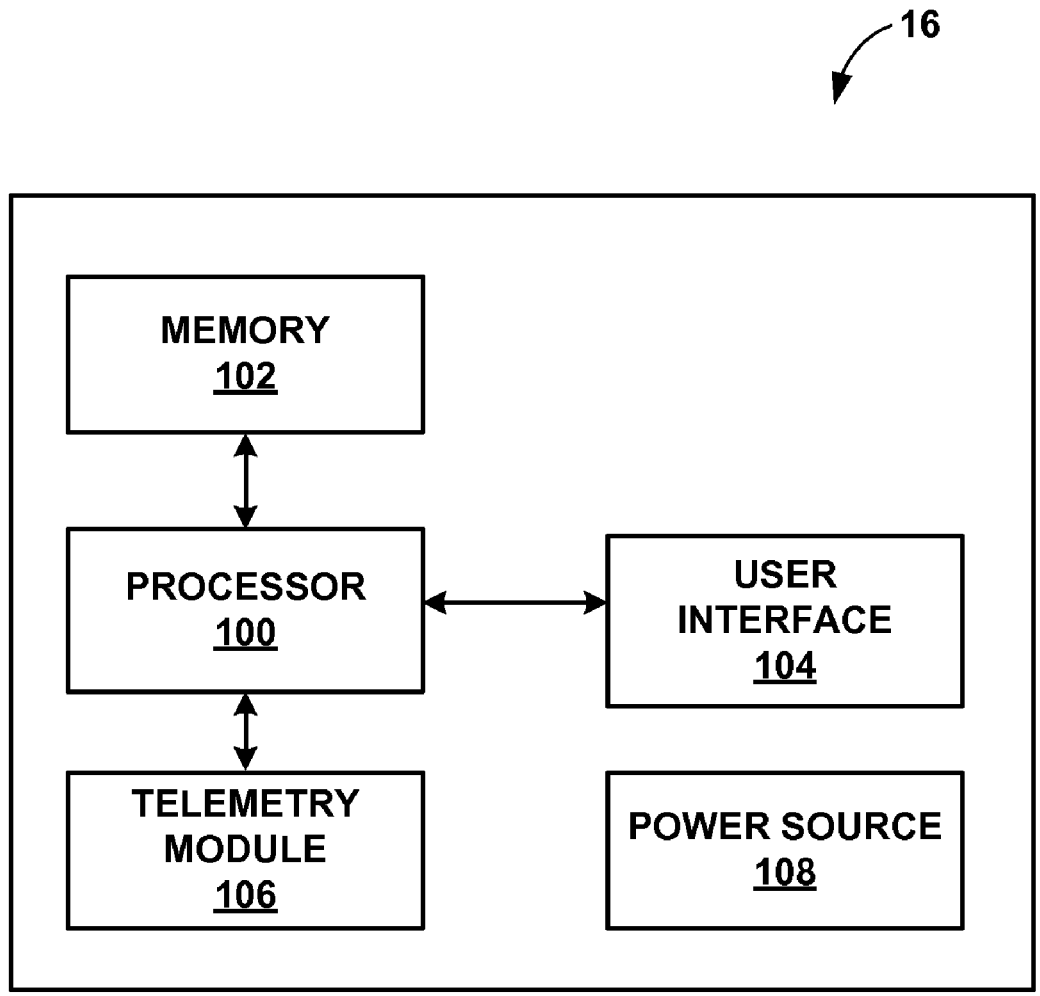
FIG. 5 is a functional block diagram of an example medical device programmer.

FIG. 5 is block diagram of an example external device 16. As shown in FIG. 5, external device 16 includes processor 100, memory 102, user interface 104, telemetry module 106, and power source 108. External device 16 may be a dedicated hardware device with dedicated software for interrogating IMD 14 to obtain information stored in memory 82 (FIG. 4), and, in some examples, for programming IMD 14. Alternatively, external device 16 may be an off-the-shelf computing device running an application that enables external device 16 to communicate with IMD 14.

A user may use external device 16 to modify the EGM and tissue perfusion sensing parameters of IMD 14. For example, the user may program the frequency at which EGM signals are sensed by EGM sensing module 86 (FIG. 4) or the minimum tissue perfusion sensing time window for sensing changes in tissue perfusion with optical perfusion sensor 22. The clinician may interact with external device 16 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to external device 16 herein, and information used by processor 100 to provide the functionality ascribed to external device 16 herein. Memory 102 may include any fixed or removable magnetic, optical, or electrical media, such as RAM, ROM, CD-ROM, hard or floppy magnetic disks, EEPROM, flash memory, or the like. Memory 102 may also include a removable memory portion that may be used to provide memory updates or increases in memory capacities. A removable memory may also allow patient data to be easily transferred to another computing device, or to be removed before external device 16 is used to program therapy for another patient.

External device 16 may communicate wirelessly with IMD 14, e.g., using RF communication or proximal inductive interaction. This wireless communication is possible through the use of telemetry module 106, which may be coupled to an internal antenna or an external antenna. An external antenna that is coupled to external device 16 may correspond to the programming head that may be placed over the implant site of IMD 14, as described above with reference to FIG. 1. Telemetry module 106 may be similar to telemetry module 88 of IMD 14 (FIG. 4).

Telemetry module 106 may also be configured to communicate with another computing device via wireless communication techniques, or direct communication through a wired connection. Examples of local wireless communication techniques that may be employed to facilitate communication between external device 16 and another computing device include RF communication according to the 802.11 or Bluetooth specification sets, infrared communication, e.g., according to the IrDA standard, or other standard or proprietary telemetry protocols. In this manner, other external devices may be capable of communicating with external device 16 without needing to establish a secure wireless connection.

Power source 108 delivers operating power to the components of external device 16. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within external device 16. In other embodiments, traditional batteries (e.g., nickel cadmium or lithium ion batteries) may be used. In addition, external device 16 may be directly coupled to an alternating current outlet to power external device 16. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Figure 6:
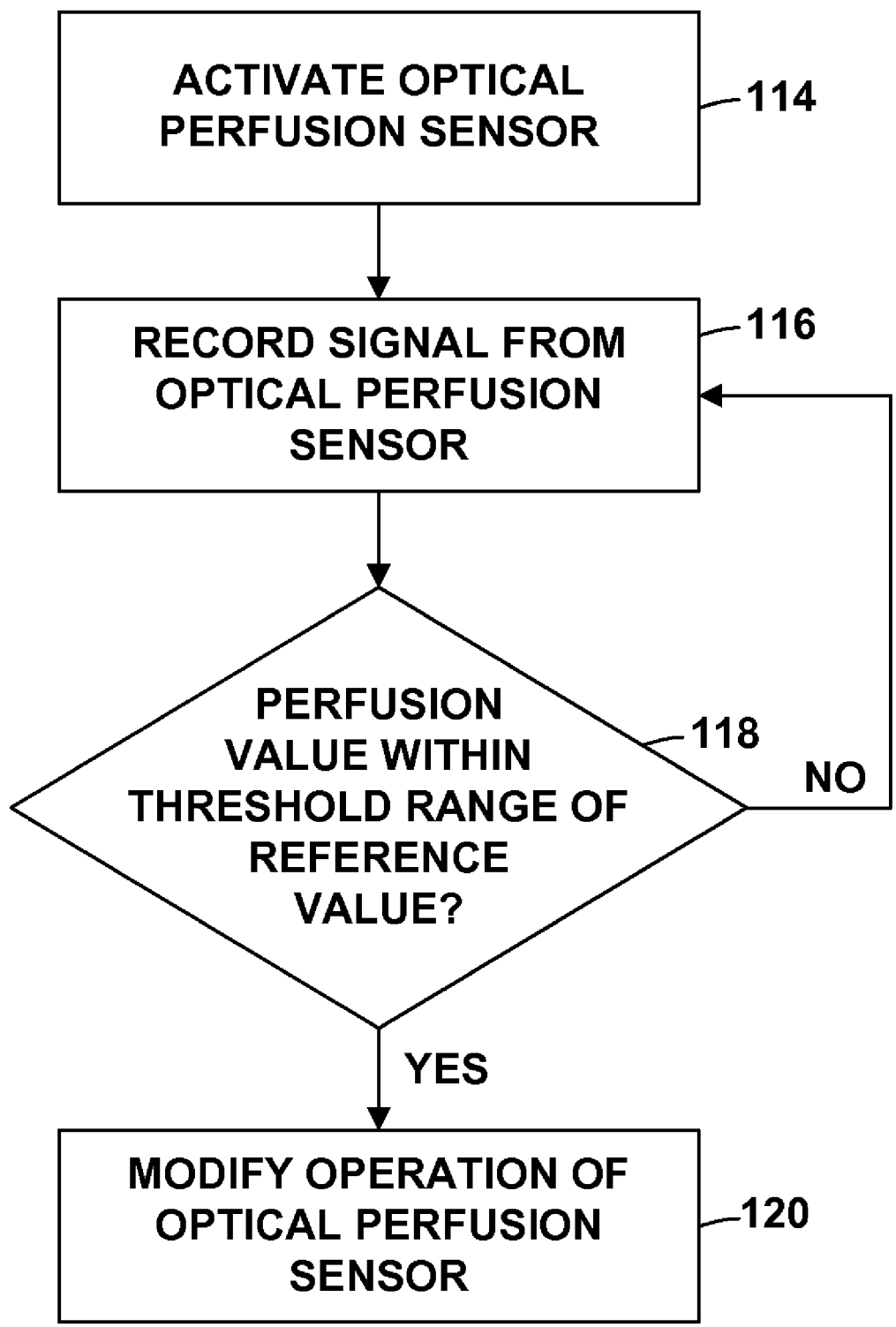
FIG. 6 is a flow diagram illustrating an example technique for collecting tissue perfusion information from an optical perfusion sensor.

FIG. 6 is a flow diagram illustrating an example technique for controlling the sensing of a blood oxygen saturation level of tissue of patient 12 by optical perfusion sensor 22. In particular, the example technique shown in FIG. 6 may be used to control when IMD 14 actively senses and records sensing and recording electrical signals from optical perfusion sensor 22. While the techniques shown in FIGS. 6-13 are with reference to components of IMD 14, in other examples, another device may perform any part of the techniques described herein. For example, a processor that is external to IMD 14 may perform any part of the techniques described herein.

In accordance with the example technique shown in FIG. 6, processor 80 may activate optical perfusion sensor 22 (114). In different examples, processor 80 may activate optical perfusion sensor 22 based on different considerations, such as whether an arrhythmia event or episode (including a plurality of events) is detected, or at predetermined intervals of time according to a predetermined schedule. An example of a technique using arrhythmia detection to trigger monitoring of tissue perfusion by optical perfusion sensor 22 is described with reference to FIG. 9. If processor 80 activates optical perfusion sensor 22 at predetermined intervals of time, the predetermined intervals of time may be stored within memory 82 of IMD 14 (FIG. 4) and processor 80 may use a clock signal to determine when optical perfusion sensor 22 should be activated. Thus, in some examples of IMD 14, processor 80 may include an internal clock or IMD 14 may include a separate clock.

In some examples, processor 80 may control red LED 60 and IR LED 62 (FIGS. 3 and 4) to emit light and detector 64 (FIGS. 3 and 4) to detect the light in order to activate perfusion sensor 22 (114). After activating optical perfusion sensor 22 (114), processor 80 may receive an electrical signal generated by detector 64 from optical perfusion sensor 22 and record the electrical signal in memory 82 of IMD 14 (116). As previously indicated, the electrical signal may be indicative of blood pressure of patient 12.

Processor 80 may determine whether a perfusion value based on the electrical signal is within a threshold range of a reference value (118). The perfusion value may be any value based on the electrical signal, and may indicate an absolute blood oxygen saturation level of the tissue that optical perfusion sensor 22 monitors, or a relative change in the blood oxygen saturation level. In some examples, the perfusion value may include a characteristic of the electrical signal, such as, for example, an amplitude or a rate of change of the electrical signal. In such examples, the reference value may be, for example, an average amplitude of an electrical signal during a particular time period, which may be determined by a clinician and stored in memory 82 (FIG. 4) of IMD 14 or may otherwise be selected.

In other examples, the perfusion value may include an O2 variation index that indicates the relative change in the blood oxygen saturation level. An O2 variation index may be calculated based on the intensity of light detected by plurality of detector elements of optical perfusion sensor 22. An O2 variation index may also be referred to as an O2 index or a optical oxygenation index. In such examples, the reference value may be an O2 variation index value that is determined based on a trend in the O2 variation index during a sample collection period. As described with reference to FIGS. 7 and 8, the sample collection period may overlap with the time at which the O2 variation index value is determined and compared to the reference value (118). In other examples, the sample collection time period for determining an O2 variation index trend may precede the time at which the O2 variation index value is determined and compared to the reference value.

The threshold range may be stored in memory 82 of IMD 14. The threshold range of a reference value that indicates acceptable blood oxygen saturation levels may be selected to be a particular percentage (%) of the reference value, such as about 5% to about 10%. In some examples, the threshold range indicates the ranges of values at which the electrical signal is considered to be substantially equal to the reference value.

If the tissue perfusion value is not within a threshold range of a reference value (118), processor 80 may continue recording the electrical signal from optical perfusion sensor 22 (116). However, if the tissue perfusion value is within the threshold range of the reference value, processor 80 may modify the operating parameters of optical perfusion sensor 22 (120). For example, processor 80 may deactivate optical perfusion sensor 22 until the next tissue perfusion monitoring period. In this manner, optical perfusion sensor 22 may be controlled to stop monitoring, which may help to conserve power resources. In some examples, the next tissue perfusion monitoring period may be, for example, automatically determined based on a predetermined schedule, such as a schedule that sets forth regular intervals for determining the blood oxygen saturation levels, or otherwise at predetermined times, which may or may not be regular intervals. In other examples, the next tissue perfusion monitoring period may be determined based on a detected physiological condition, such as a detected cardiac arrhythmia event or episode, as described with respect to FIG. 9.

In some examples, processor 80 may control at least one of red LED 60 and IR LED 62 to cease emitting light in order to deactivate optical perfusion sensor 22. For example, processor 80 may monitor blood oxygen saturation levels with red LED 60. As another example, processor 80 may modify the operating parameters of optical perfusion sensor 22 (120) by controlling optical perfusion sensor 22 to monitor tissue perfusion at a different frequency. For example, processor 80 may decrease the frequency with which optical perfusion sensor 22 actively monitors the oxygen saturation level of the blood of patient 12.

Figure 7:
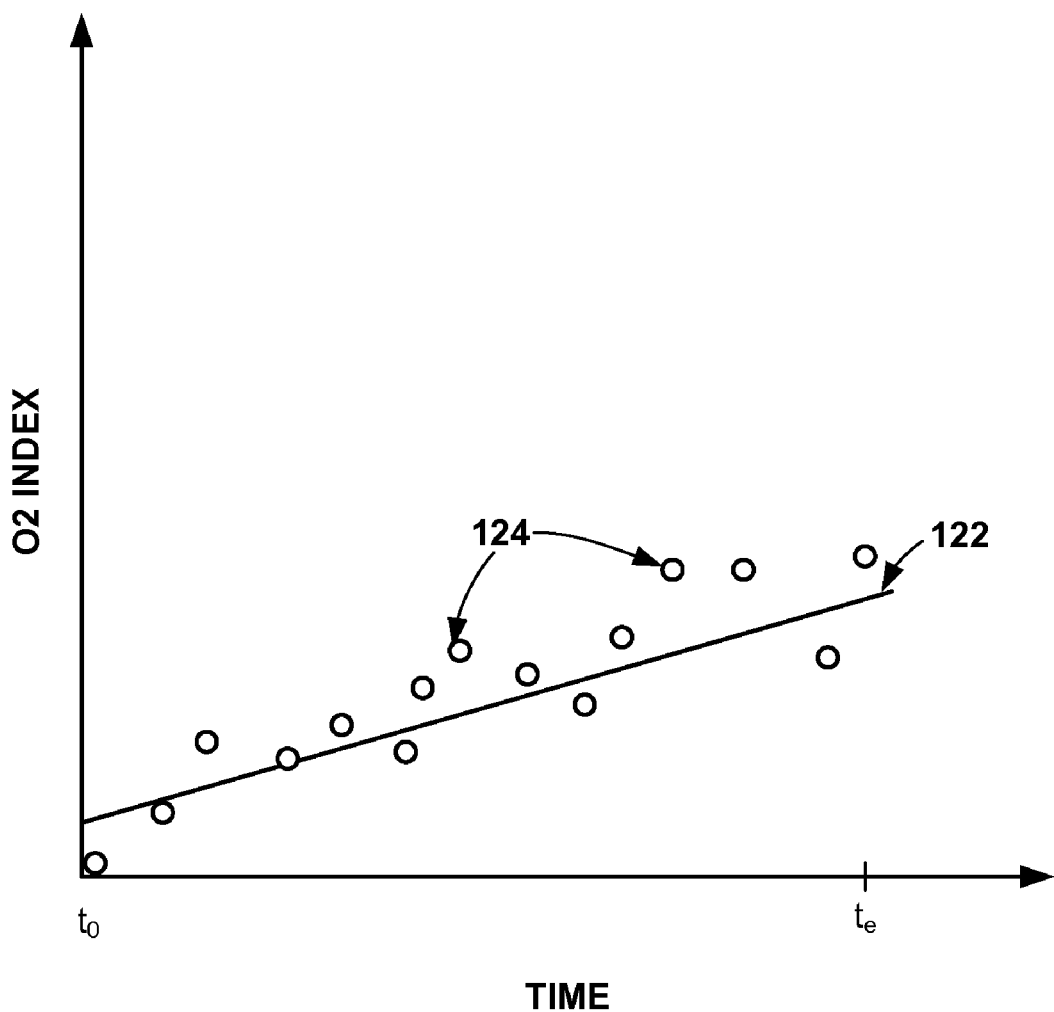
FIG. 7 is an example graph illustrating optical oxygenation (O2) variation index values over time and an O2 variation index trend determined based on the O2 variation index values.

FIG. 7 is a graph that illustrates an O2 variation index trend 122 and various O2 variation index values 124 determined based on an electrical signal from detector 64 of optical perfusion sensor 22. The O2 variation index values 124 may be determined based on the intensity readings associated with the intensity of the red light emitted by red LED 60 and the IR light emitted by IR LED 62 that is received by detector 64 at a particular time. In addition, the O2 variation index trend 122 may be determined based on O2 variation index values 124 during a sample collection period. As previously indicated, changes in blood oxygen saturation levels of the tissue monitored by optical perfusion sensor 22 may be determined based on the O2 variation index trend 122.

In one example, to determine the O2 variation index trend 122, both a red light baseline intensity $i_0$ and an infrared light baseline intensity $i*_0$ are identified from sample outputs of detector 64 received at a predetermined sample rate over a sampling time interval. For example, in one example, detector 64 may receive sample outputs from red LED 60 and IR LED 62 at a sampling rate of three samples per second over a two second sampling time interval. Baseline intensity $i_0$ and baseline intensity $i*_0$ are then determined from the sample outputs from red LED 60 and IR LED 62, respectively. For example, according to an embodiment of the present invention, baseline intensity $i_0$ and baseline intensity $i*_0$ are determined, respectively, by setting baseline intensity $i_0$ equal to the average of the sample outputs from red LED 60 over a predetermined time period and setting baseline intensity $i*_0$ equal to the average of the sample outputs from IR LED 62 over the predetermined time period.

Once the red and IR baseline intensities $i_0$ and $i*_0$, respectively, have been determined, processor 80 of IMD 14 may determine a variation index for subsequently received signals from detector 64, from which the intensity of red light and IR light sensed by detector 64 may be determined, e.g., using the demodulating technique described above. As described in U.S. Patent Application Publication No. 2007/0239053 to Bhunia, processor 80 may use the following oxygen variation index equation to determine the O2 variation index for a particular signal output of detector 64:

$$O2 \text{ Variation Index} = (i/i_0) - (i*/i*_0)$$

In the above-referenced equation for determining O2 variation index, "i" is the intensity of red light from red LED 60 incident on detector 64 for a given sample collection period and "i*" is the intensity of IR light from IR LED 62 incident on detector 64 for the same sample collection period. According to the equation provided above, the O2 variation index for each two-wavelength sample output is the difference between the proportion of the red and the IR intensity signals with respect to their corresponding baseline intensities. Using the example sampling rate of about 3 Hertz (Hz), three variation indices may be generated each second, which may be used to determine the O2 variation index trend 122.

Other equations for calculating an O2 variation index may be used. For example, if the proportion of the red intensity signal to the baseline red intensity $(i/i_0)$ is referred to as the normalized red intensity and the proportion of the IR intensity signal to the baseline IR intensity $(i*/i*_0)$ is referred to as the normalized IR intensity, O2 variation index may be substantially equal to a ratio of the normalized red and IR intensities, or may be a difference between unequally weighted red and IR normalized intensities.

Figure 8:
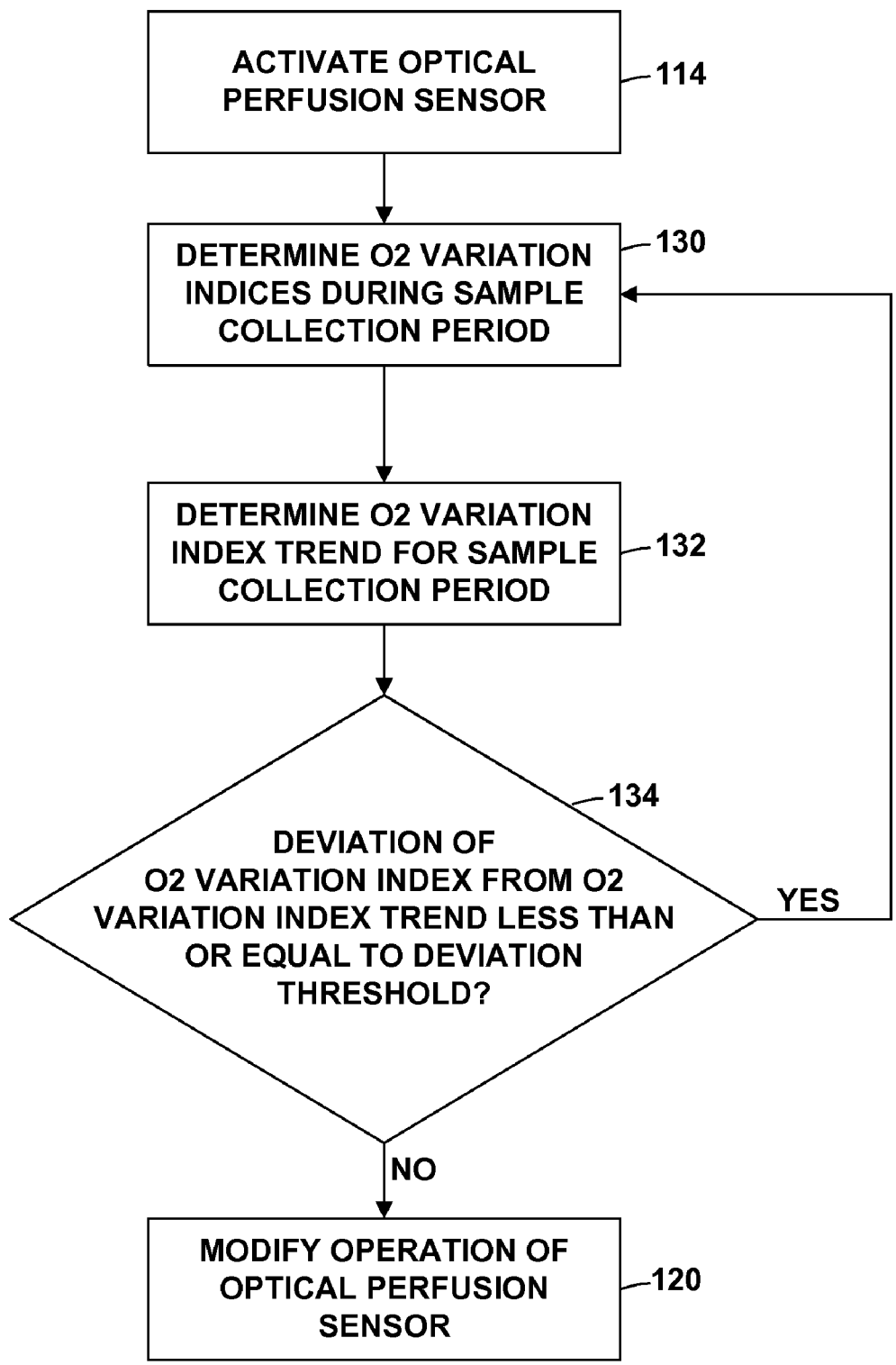
FIG. 8 is a flow diagram illustrating an example technique for determining a time period for collecting tissue perfusion information from an optical perfusion sensor based on O2 variation index values.

FIG. 8 is flow diagram illustrating example technique for determining a time period for actively monitoring oxygen saturation levels of tissue with optical perfusion sensor 22. In FIG. 8, optical perfusion sensor 22 may be activated (114), and processor 80 may determine a plurality of O2 variation indices based on the electrical signal from detector 64 during a sample collection period (130). As previously indicated, the intensity of red light detected by detector 64 and the intensity of IR light detected by detector 64 may be extracted from a single electrical signal generated by detector 64 or detector 64 may output two separate signals indicative of a respective one of the detected red light and IR light.

Processor 80 may receive the electrical signal from detector 64 and determine a plurality of O2 variation indices for a predetermined sample collection period (130). The predetermined sample collection period may be set as a predetermined period of time, such as about 5 seconds or may be set as a predetermined number of samples, such as about 15 O2 variation index samples, which may be collected at any frequency, such as about 2 Hz to about 10 Hz. In some examples, the predetermined sample collection period may be selected by a clinician or another user. In some examples, processor 80 may begin computing O2 variation indices 124 (FIG. 7) using the optical sample inputs from optical sensor 22 at multiple wavelengths (e.g., a red wavelength and an IR wavelength) and the equation provided above with respect to FIG. 7.

At the end of the sample collection period, processor 80 may determine an O2 variation index trend for the sample collection period (132). In one example, to determine the O2 variation index trend, processor 80 may set any previous trends to zero. In one example, a sample rate of about 3 Hz is utilized and the sample collection period is set as approximately five seconds, for example, so that 15 O2 variation indices 124 are determined over each sample collection period. In one example, in order to determine the O2 variation index trend, processor 80 may measure a variation of each of the acquired O2 variation indices 124 (FIG. 7) occurring during the sample collection period.

Processor 80 may determine the O2 variation index trend 122, e.g., by performing a least square linear fit of the acquired O2 variation indices 124 during the sample collection period. The resulting O2 variation index trend 122 trend may have a start point at time $t_0$ (FIG. 7) when the first O2 variation index was determined, and an endpoint at time $t_e$ (FIG. 7) when the last O2 variation index value was determined for the sample collection period. In other examples, the O2 variation index trend 122 may be obtained, for example, by an alternative filtering technique and the measure of the deviation of the O2 variation indices 124 from the O2 variation index trend 122 may be determined as the mean square of the indices 124 from the filtered index trend.

After processor 80 determines the O2 variation index trend 122 for the sample collection period, processor 80 may determine whether any of the O2 variation indices deviate from the O2 variation index by less than or equal to a deviation threshold (134). As previously indicated, the deviation threshold may be stored within memory 82 (FIG. 4) of IMD 14. The deviation threshold may indicate a change in an O2 variation index value that indicates a potentially abnormal change in blood oxygen saturation levels. That is, the deviation threshold may indicate a change in blood oxygen saturation level that may be associated with a patient event, such as a syncope or cardiac arrhythmia. In some examples, processor 80 may determine a deviation of the O2 variation index values 124 during the sample collection period from the O2 variation index trend 122 by determining the mean square deviation of the O2 variation indices 124 in the current window of O2 variation indices from the O2 variation index trend 122.

If the deviation of any of the O2 variation indices 124 from the O2 variation index trend 122 for the current sample collection period less than or equal to the deviation threshold, processor 80 may determine that the O2 variation index was relatively stable and within an acceptable range of oxygen saturation level variation, and may modify the operation of optical perfusion sensor 22 (120). On the other hand, if the deviation of any of the O2 variation indices 124 from the O2 variation index trend 122 for the current sample collection period exceeds the deviation threshold, processor 80 may determine that the oxygen saturation levels of the tissue indicate a patient event may be occurring. Processor 80 may determine the O2 variation indices 124 for a subsequent sample collection period (130), and determine the O2 variation index trend 122 for the subsequent sample collection period (132), and determine a deviation of the O2 variation indices 124 from the trend 122 (134) until the deviation is less than or equal to the deviation threshold value. At that time, processor 80 may change the operation of optical perfusion sensor 22 (120), e.g., by deactivating active tissue perfusion sensing by sensor 22.

Figure 9:
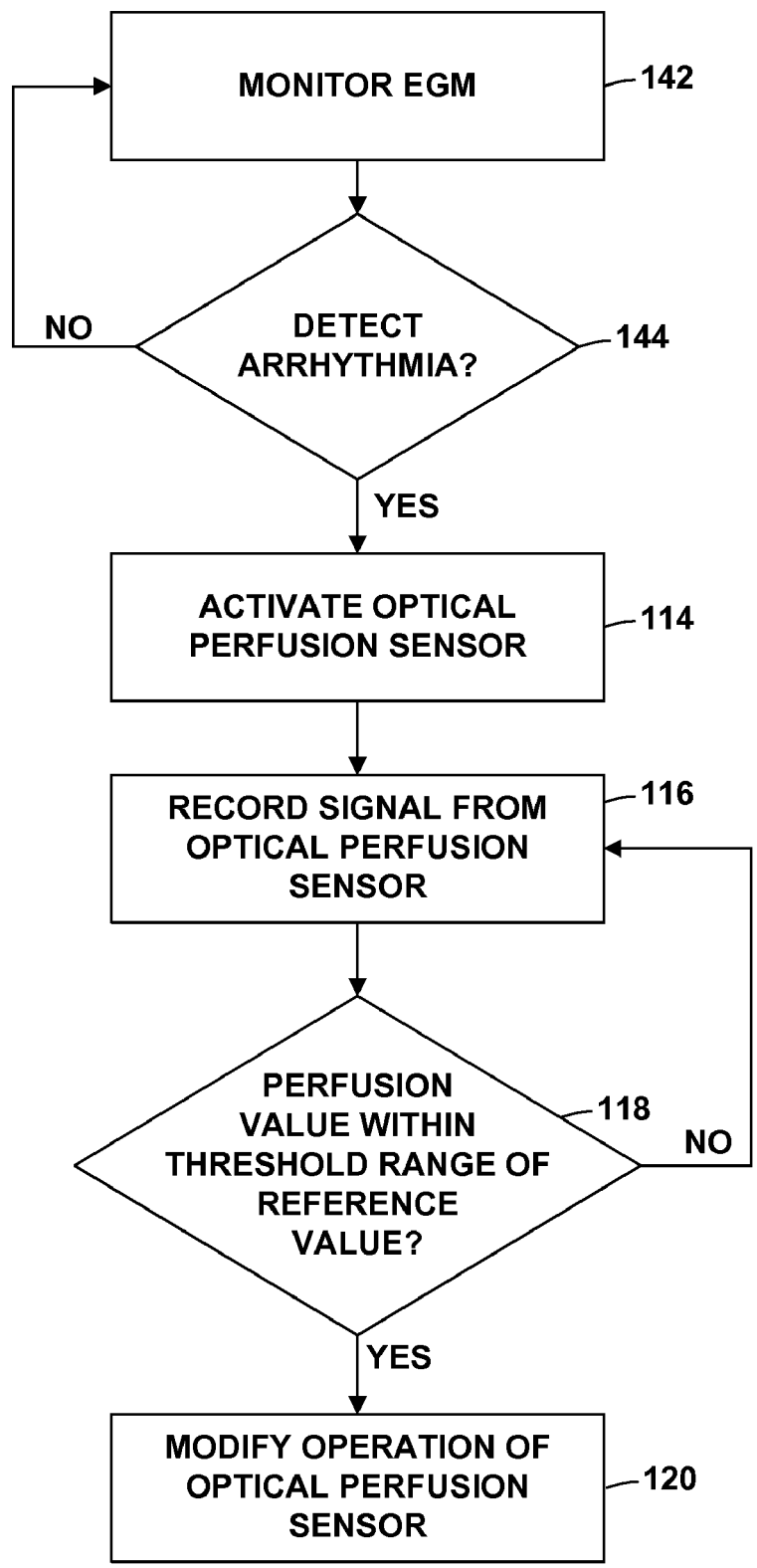
FIG. 9 is a flow diagram illustrating an example technique for collecting tissue perfusion information from an optical perfusion sensor in response to detecting a cardiac arrhythmia.

As previously discussed, optical perfusion sensor 22 may be activated using different techniques. FIG. 9 is a flow diagram illustrating another example technique for sensing and recording electrical signals from optical perfusion sensor 22, whereby optical perfusion sensor 22 is activated in response to detecting a cardiac arrhythmia event or episode (e.g., including more than one event). While cardiac arrhythmia events are primarily referred to in the description of FIG. 9, in other examples, the technique shown in FIG. 9 may be used to active optical perfusion sensor 22 in response to detecting an arrhythmia episode. In some examples, processor 80 may detect an arrhythmia episode by determining whether a particular number of arrhythmia events are detected.

Processor 80 may monitor an EGM that indicates electrical activity of heart 32 (FIG. 2) of patient 12 (142). In some examples, processor 80 monitors the EGM by receiving a signal from EGM sensing module 86 (FIG. 4). Processor 80 may detect a cardiac arrhythmia event based on the EGM signal using any suitable technique (144). Examples of cardiac arrhythmia events include an asystole, a bradycardia event, a ventricular fibrillation event, a ventricular tachycardia event or a fast ventricular tachycardia event.

In some examples, processor 80 may detect a cardiac arrhythmia event by determining a duration of a cardiac cycle and comparing the duration to a threshold value. As previously discussed, a cardiac cycle duration may be, for example, measured between successive R-waves or P-waves of the EGM signal. Different threshold durations may be used to characterize a heart cycle as a bradycardia event, a ventricular fibrillation event, a ventricular tachycardia event or a fast ventricular tachycardia event. The threshold duration values for determining whether an R-R interval or a P-P interval qualifies the cardiac cycle as a particular arrhythmia event may be stored within memory 82 of IMD 14. In other examples, processor 80 may use other techniques for detecting an arrhythmia event.

If processor 80 does not detect a cardiac arrhythmia event, processor 80 may continue monitoring EGM (142). Upon detecting the arrhythmia event (144), processor 80 may activate optical perfusion sensor 22 (114). Processor 116 may receive an electrical signal generated by detector 64 from optical perfusion sensor 22 and record the electrical signal in memory 82 of IMD 14 and/or may record perfusion values derived from the electrical signal in memory 82 (116).

Just as with the technique described with respect to FIG. 6, processor 80 may determine whether a perfusion value that is based on the electrical signal is within a threshold range of a reference value (118). If the perfusion value is not within a threshold range of a reference value (118), processor 80 may continue recording the electrical signal from optical perfusion sensor 22 (116). However, if the perfusion value is within the threshold range of the reference value, processor 80 may modify the operation of optical perfusion sensor 22 (120). In some examples, processor 80 may control red LED 60 and IR LED 62 to cease emitting light in order to deactivate optical perfusion sensor 22 (120).

Figure 10:
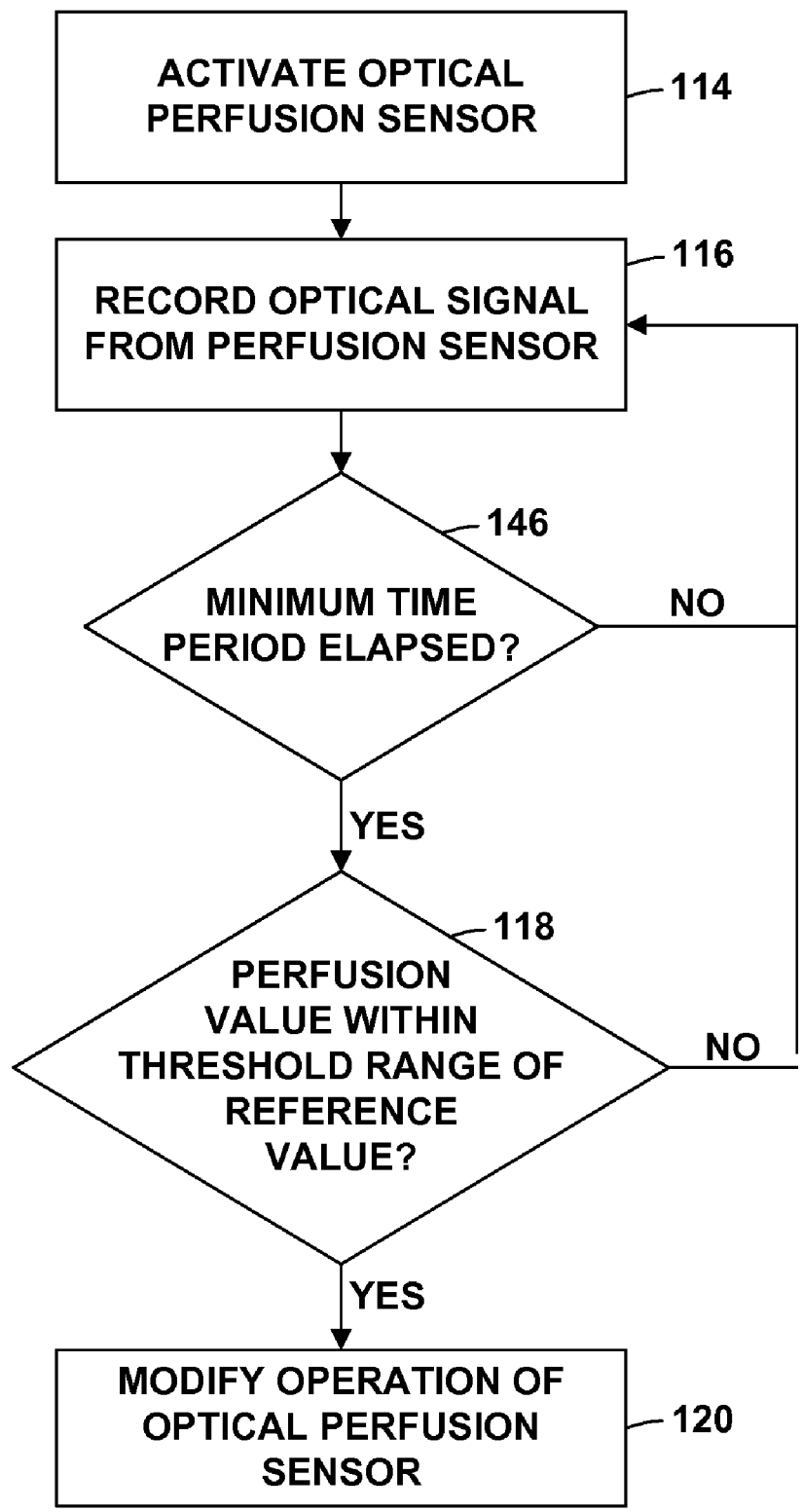
FIG. 10 is a flow diagram illustrating another example technique for collecting tissue perfusion information.

FIG. 10 is a flow diagram illustrating another example technique for sensing and recording electrical signals from optical perfusion sensor 22. Upon activating optical perfusion sensor (114) and recording the electrical signal from detector 64 or perfusion values derived from the signal (116), as described with reference to FIG. 6, processor 80 may determine whether a predetermined minimum period of time has elapsed (146). The minimum period of time may be stored within memory 82 of IMD 14 (FIG. 4). The minimum period of time may indicate a minimum duration of time during which signals from perfusion sensor 22 are sensed and recorded. Thus, in the technique shown in FIG. 10, the tissue perfusion information collected by IMD 14 may be collected in increments of time that are at least equal to the predetermined minimum period of time.

As previously described, a drop in blood oxygen saturation levels indicated by the signal from optical perfusion sensor 22 may not be immediately observed following the detection of a cardiac arrhythmia event or episode. The minimum period of time may be selected to detect the delayed change in tissue perfusion, if any, that may be observed following a detected cardiac event or episode. Accordingly, the minimum duration of time in which IMD 14 collects and records tissue perfusion information may be useful for storing a sufficient amount of information about the blood oxygen saturation level of tissue for a clinician to evaluate the patient's physiological condition.

Increasing the minimum period of time may help increase the sensitivity of optical perfusion sensor 22 in detecting changes in the oxygen saturation level of blood-perfused tissue. Increasing the minimum period of time may increase the detection window for detecting a change in the blood oxygen saturation level. As discussed above, however, increasing the detection window may decrease the specificity with which optical perfusion sensor 22 detects changes in the oxygen saturation level of blood-perfused tissue. In some examples, the minimum period of time for collecting and storing signals from optical perfusion sensor 22 may be about 8 seconds to about 10 seconds. However, other minimum periods of time are contemplated. In some cases, a minimum period of time of about 8 seconds to about 10 seconds may result in specificity of about 90%.

In some examples, the minimum duration of time period of time for collecting and storing signals from optical perfusion sensor 22 may be programmable. Different patients may exhibit different tissue perfusion activity, and, therefore, the detection window for detecting a change in tissue perfusion may differ based on the particular patient. By enabling a clinician to select the predetermined minimum period of time and program the minimum period of time into IMD 14, a clinician may personalize the detection window to the particular patient.

Monitoring and recording the electrical signal from optical perfusion sensor 22 for a duration of time that is based on whether a perfusion value that is derived from the electrical signal is within a threshold range of a reference value may be useful. However, in some examples, the perfusion value may return to within a threshold range of a reference value relatively quickly. In such circumstances, IMD 14 may provide relatively little tissue perfusion information. Thus, recording tissue perfusion information for at least a predetermined minimum time period may help increase the amount of tissue perfusion information that is stored by IMD 14, which may help provide a clinician with a better picture of the patient's physiological condition.

If the minimum period of time has not elapsed (146), processor 80 may continue controlling the monitoring and recording of the electrical signal from optical perfusion sensor 22 (116). On the other hand if the minimum period of time has elapsed, processor 80 may determine whether a perfusion value that is based on the electrical signal is within a threshold range of a reference value (118). As previously indicated, the perfusion value may indicate the absolute blood oxygen saturation level of the tissue monitored by optical perfusion sensor 22 or a relative change in the blood oxygen saturation level.

If the perfusion value is not within the threshold range of the reference value, processor 80 may continue monitoring and recording the electrical signal from optical perfusion sensor 22 (116), even if the minimum time period has elapsed. The minimum period of time indicates a minimum duration during which optical perfusion sensor 22 senses tissue perfusion and during which processor 80 records the electrical signal from sensor 22. Thus, processor 80 may monitor and record the electrical signal for a duration longer than the minimum period of time.

The technique shown in FIG. 10 is useful for efficiently generating and storing useful tissue perfusion information, e.g., tissue perfusion information that may be associated with a cardiac arrhythmia event or episode, or tissue perfusion information that may indicate a physiological condition of the patient that merits further diagnoses or therapy. Rather setting an arbitrary perfusion monitoring time period, the technique shown in FIG. 10 sets a minimum threshold time period that is relatively short (e.g., less than one minute), while still enabling processor 80 to monitor and store electrical signals that occur outside of the minimum period of time.

Figure 11:
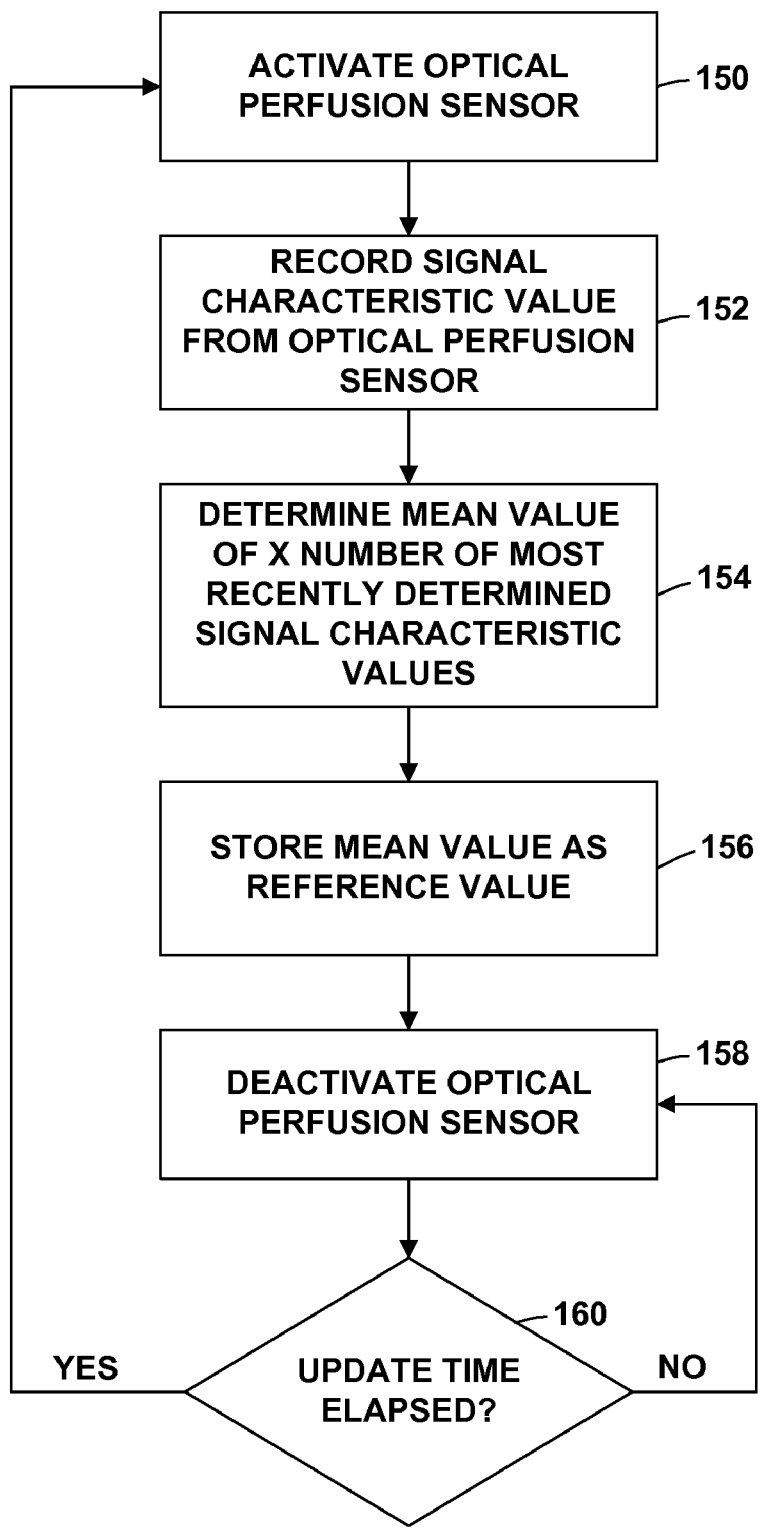
FIG. 11 is a flow diagram illustrating an example technique for generating a reference value that may be used to determine a tissue perfusion information collection time window.

FIG. 11 is a flow diagram illustrating an example technique for generating a reference value based on an electrical signal characteristic, such as a voltage or current amplitude. The reference value may be used to determine a tissue perfusion information collection time window, e.g., as described with reference to FIGS. 6, 9, and 10. As described with reference to FIGS. 6, 9, and 10, processor 80 of IMD 14 may control optical perfusion sensor 22 to collect and store tissue perfusion information (e.g., electrical signals indicative of the detected red light and IR light) until a perfusion value that is based on the electrical signal generated by detector 64 of optical perfusion sensor 22 is within a predetermined range of a reference value. A determination that the perfusion value is within a predetermine range of a reference value may indicate, for example, that the patient's blood pressure has stabilized and/or returned to a normal value in which a cardiac arrhythmia or syncopic event is not observed. The technique shown in FIG. 11 may be independent of the techniques for collecting and recording tissue perfusion information shown in FIGS. 6, 9, and 10. In particular, the technique shown in FIG. 11 may be used in addition to the techniques for collecting and recording tissue perfusion information described herein.

Processor 80 may activate optical perfusion sensor 22 (150) and record the electrical signal generated by detector 64 or a perfusion value derived from the signal, such as an O2 variation index (152). In some examples, optical perfusion sensor 22 may already be activated. For example, processor 80 may update the reference value using the technique shown in FIG. 11 while optical perfusion sensor 22 is actively recording data in response to some detected cardiac arrhythmia event or episode or in response to a predetermined schedule. If processor 80 has collected previous perfusion values, processor 80 may determine a mean value of at least X number of the most recently determined signal characteristic values. The number of signal characteristic values used to determine the mean value (i.e., the number indicated by the variable "X") may be selected by a clinician and stored in memory 82 of IMD 14.

The calculated mean value may be stored as the reference value in memory 82 (156). After determining and storing the reference value, processor 80 may deactivate optical perfusion sensor 22 (158). However, in other examples, optical perfusion sensor 22 may remain active and processor 80 may continue collecting and storing electrical signals from detector 64 in accordance with the technique shown in FIG. 6, 9 or 10. This may occur if the reference value update occurs while optical perfusion sensor 22 is actively recording data in response to some detected cardiac arrhythmia event or episode or in response to a schedule.

Processor 80 may periodically update the stored reference value. In the technique shown in FIG. 11, processor 80 updates the stored reference value at a time interval determined by an update time, which may be stored within memory 82. The update time may be selected by a clinician or otherwise selected, and may be selected to generate a useful reference value that reflects normal tissue perfusion values of patient 12. A normal tissue perfusion value may be, for example, the tissue perfusion value of patient 12 that occurs during a normal heart rhythm of patient 12.

After generating and storing a reference value (156), processor 80 may determine whether the update time has elapsed (160). Processor 80 may not update the reference value until the update time has elapsed. If the update time has elapsed (160), processor 80 may activate optical perfusion sensor 22 (150), if necessary, and record a signal characteristic value (152) to determine a mean value (154). The technique shown in FIG. 11 may be repeated at predetermined times, which may be reflected by the update time interval or by a predetermined schedule that does not necessarily set regular intervals for updating the reference value.

Figure 12:
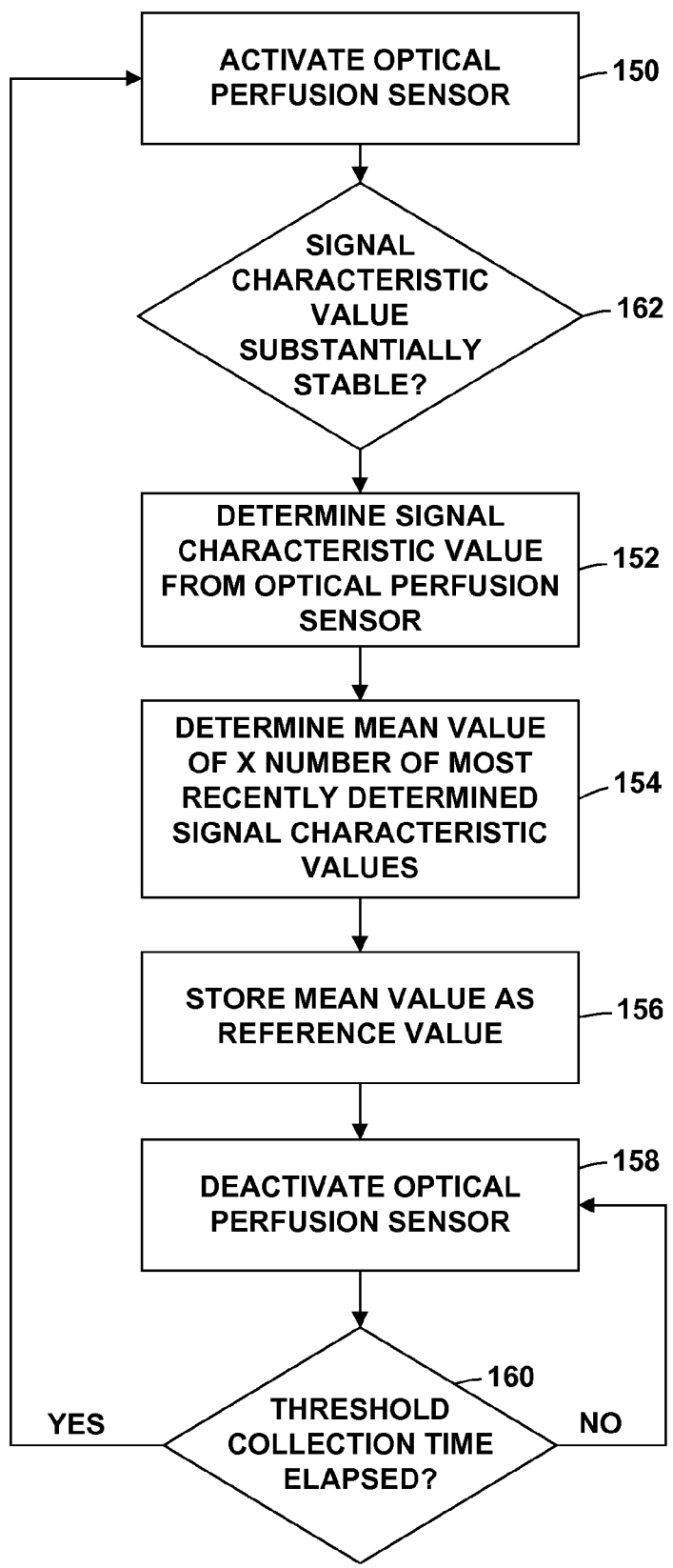
FIG. 12 is a flow diagram illustrating another example technique for generating a reference value that may be used to determine a tissue perfusion information collection time window.

FIG. 12 is a flow diagram illustrating another example technique for generating a reference value that may be used to determine a tissue perfusion information collection time window. The technique shown in FIG. 12 is similar to that shown in FIG. 11. However, prior to determining a signal characteristic value (152) that is used to determine the mean value, processor 80 may determine whether the signal characteristic is substantially stable (162).

Processor 80 may determine whether the signal characteristic is substantially stable using any suitable technique. In one example, the signal characteristic may be an amplitude of the electrical signal generated by detector 64 and processor 80 may determine that the amplitude of the electrical signal is substantially stable if the amplitude at a selected time varies by no more than a threshold range relative to the average amplitude value of the electrical signal during a predetermined time period preceding the selected time. The predetermined time period for calculating the average amplitude may be determined by a clinician or otherwise selected. In some examples, the predetermined time period may be a time window of about 3 seconds to about 10 seconds, such as about 4 seconds. The time window may be a moving time window such that the average amplitude value is a moving average. The threshold range may be determined by a clinician or otherwise selected. In some examples, the threshold range may be about 1% to about 15%, such as about 10%.

In another example, processor 80 may determine that the amplitude of the electrical signal is substantially stable if the difference between the amplitude value and a mean or median of the amplitude values during a predetermined time period is within a threshold range. The differences may be absolute. In other examples, processor 80 may determine that the amplitude of the electrical signal is substantially stable if the mean or median value of the differences between a plurality of sequential amplitude values and a mean or median of the amplitude values during a predetermined time period are within a threshold range.

In some examples, cardiac signal information may be collected based on detected blood oxygen saturation level or another tissue perfusion value derived from the blood oxygen saturation level. For example, processor 80 of IMD 14 may control EGM sensing module 86 (FIG. 4) to monitor an EGM or ECG upon detecting a threshold change in blood oxygen saturation levels of patient 12 based on one or more electrical signals generated by optical perfusion sensor 22. Selective activation of EGM sensing module 86 may help conserve energy (e.g., power source 90), while still sensing and storing useful cardiac signal information within memory 82.

Figure 13:
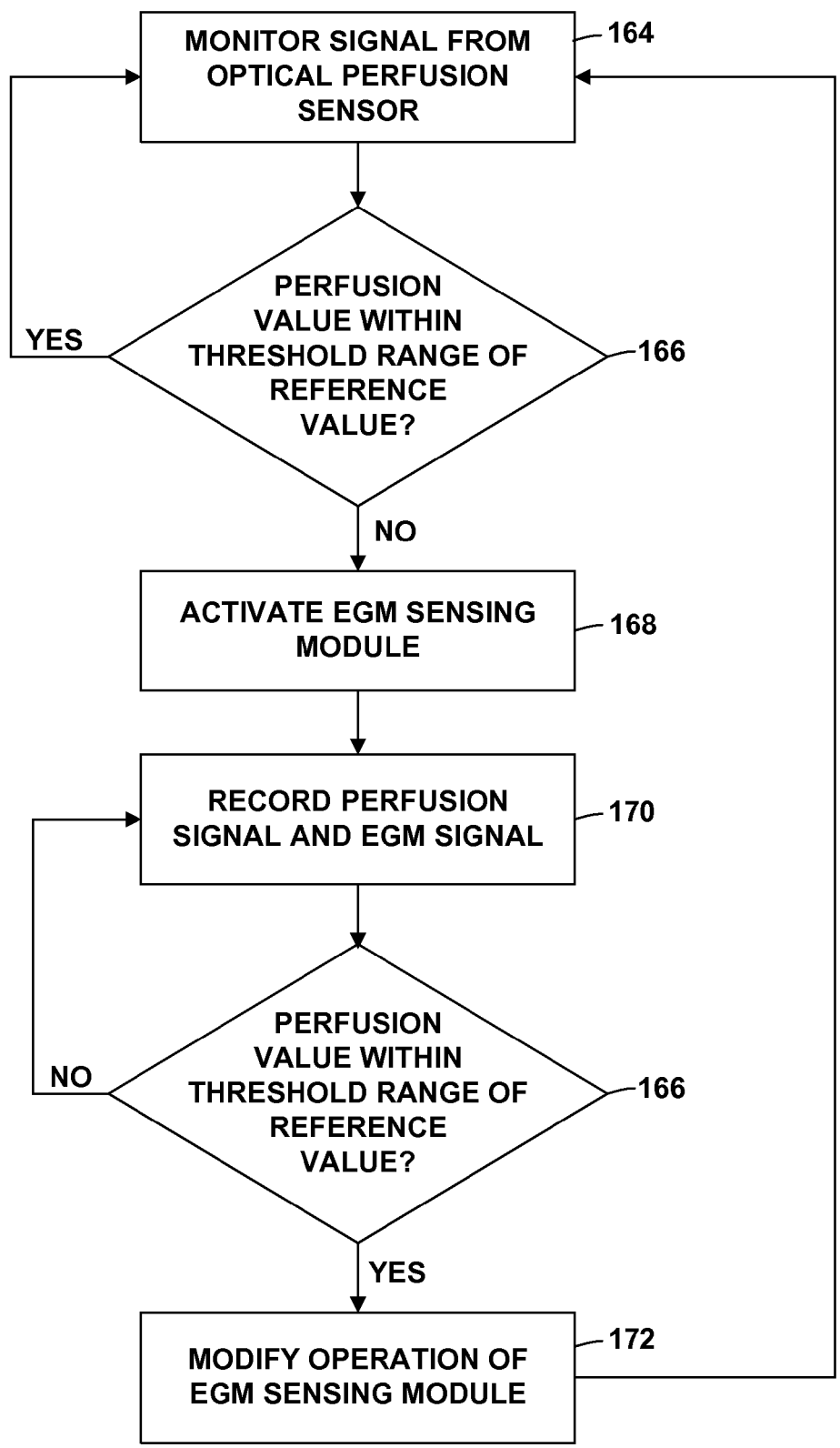
FIG. 13 is a flow diagram illustrating an example technique for collecting cardiac signal information in response to detecting a tissue perfusion level outside of a threshold range.

FIG. 13 is a flow diagram illustrating an example technique for collecting EGM information based on tissue perfusion information. In the example shown in FIG. 13, optical perfusion sensor 22 continuously or periodically senses the oxygenation level of the blood in the tissue proximate to red LED 60, IR LED 62, and detector 64 (FIGS. 3 and 4). Processor 80 of IMD 14 may monitor the electrical signal generated by detector 64 (164). Processor 80 may determine whether a perfusion value based on the electrical signal is within a threshold range of a reference value (166), e.g., using the techniques described above with respect to FIGS. 6, 9, and 10. If the perfusion value is within a threshold range of a reference value (166), processor 80 may continue monitoring the signal from optical perfusion sensor 22 (164). A perfusion value within a threshold range of a reference value may indicate that the patient's blood pressure is relatively normal or stable. That is, a blood oxygen saturation level within a predetermined range of values may indicate that the patient's hemodynamic activity has not changed by an undesirable amount, such as change that may indicate a patient condition is present. The patient condition may be, for example, the occurrence of a syncopic event or a cardiac arrhythmia, or a physiological state in which a syncopic event or a cardiac arrhythmia is likely to occur.

If the perfusion value falls outside of the threshold range of the reference value (166), processor 80 may determine that a patient condition may be present. In order to obtain physiological information that provides a better picture of the patient's physiological condition at the time the change in the perfusion value was detected, and generate information that a clinician may later use to diagnose patient 12 or information that IMD 34 (FIG. 2) may use to deliver therapy to patient 12, processor 80 may modify an operation of EGM sensing module 86 (FIG. 4). That is, processor 80 may control EGM sensing module 86 based on a perfusion value.

In the example shown in FIG. 13, processor 80 may activate EGM sensing module 86 if the perfusion value falls outside the threshold range of the reference value (168). Processor 80 may record the signal from optical perfusion sensor 22 and EGM sensing module 86 in memory 82 (FIG. 4) (170). In this way, processor 80 may record tissue perfusion information (e.g., blood oxygen saturation levels) and associated cardiac signal information in response to a detecting a perfusion value that is outside of a threshold range of a reference value. The cardiac signal information may indicate the cardiac activity of patient 12 at the time the change in tissue perfusion was detected.

As with activation of optical perfusion sensor 22, "activation" of EGM sensing module 86, reference to "activating" EGM sensing module 86 in response to certain events or in accordance with a schedule may refer to the active storing of signals from EGM sensing module 86 within memory 82 of IMD 14, rather than the powering on and off of EGM sensing module 86. However, in some examples, EGM sensing module 86 may be powered on when active cardiac signal sensing by EGM sensing module 86 is activated, and then powered off following a predetermined duration of time or upon the return of the blood oxygen saturation level of the patient to a particular value. In the example shown in FIG. 13, when EGM sensing module 86 is not activated, e.g., when the perfusion sensing triggers have not occurred, IMD 14 may not actively record signals from EGM sensing module 86.

Processor 80 may continue sensing and recording the tissue perfusion information from optical perfusion sensor 22 and EGM signals from EGM sensing module 86 in memory until the signal from optical perfusion sensor 22 returns to a threshold range of a reference value (166). This may indicate that the patient's blood pressure returned to a stable value and that symptoms of the patient condition (e.g., syncope or cardiac arrhythmia) have likely ceased. After determining that the signal from optical perfusion sensor 22 returns to a threshold range of a reference value, processor 80 may modify the operating parameters of EGM sensing module 86 (172). In some examples, processor 80 may change the operating parameters of EGM sensing module 86 by deactivating EGM sensing module 86 or by controlling EGM sensing module 86 to monitor the electrical activity of heart 32 (FIG. 2) at a lower frequency. This may help conserve the available power of power source 90 of IMD 14.

In other examples, processor 80 may control the operation of EGM sensing module 86 based on information from optical perfusion sensor 22 using other techniques. For example, processor 80 may control EGM sensing module 86 to periodically monitor the cardiac signals of patient 12. Processor 80 may store the cardiac signals sensed by EGM sensing module 86. Upon detecting a perfusion value that falls outside of the threshold range of the reference value (166), processor 80 may increase the frequency with which EGM sensing module 86 monitors the cardiac signals of patient 12 and the frequency with which processor 80 stores the cardiac signals from EGM sensing module 86. Patient motion may affect the signal generated by optical perfusion sensor 22. For example, as patient 12 moves, the interface between optical perfusion sensor 22 and the adjacent tissue may change, thereby changing the proximity to vasculature, as well as the density of the adjacent tissue. This may result in a large change in detected blood oxygen saturation levels, which may not accurately reflect the blood oxygen saturation activity. In each of the examples described above, an algorithm for detecting and reducing noise from factors such as patient motion may be implemented. Example techniques for reducing the effects of noise on the signal generated by an optical perfusion sensor is described in U.S. Patent Application Publication No. 2007/0239215 to Bhunia et al., entitled, "METHOD AND APPARATUS FOR USING AN OPTICAL HEMODYNAMIC SENSOR TO IDENTIFY AN UNSTABLE ARRHYTHMIA," which was previously incorporated by reference.

The techniques described in this disclosure, including those attributed to IMD 14, external device 16, IMD 34, programmer 42, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various embodiments of the invention have been described. These and other embodiments are within the scope of the following claims.

The invention claimed is:

1. A method comprising:
   receiving an electrical signal from an optical perfusion sensor, wherein the electrical signal is indicative of blood oxygen saturation of tissue of a patient; and
   modifying an operation of a cardiac signal sensing module that senses electrical activity of a heart of the patient based on a perfusion value that is based on the electrical signal, wherein modifying the operation of the cardiac signal sensing module comprises activating the cardiac signal sensing module to sense electrical activity of the heart.

2. The method of claim 1, wherein the cardiac signal sensing module is configured to monitor an electrogram or electrocardiogram signal.

3. The method of claim 1, further comprising determining whether the perfusion value that is based on the electrical signal is within a threshold range of values, wherein activating the cardiac signal sensing module to monitor electrical activity of the heart comprises activating the cardiac signal sensing module if the perfusion value is not within the threshold range of values.

4. The method of claim 3, wherein modifying the operation of the cardiac signal sensing module further comprises modifying the operation of the cardiac signal sensing module if the perfusion value is within the threshold range of values.

5. The method of claim 4, wherein the electrical signal comprises a first electrical signal and the cardiac signal sensing module generates a second electrical signal indicative of the electrical activity of the heart, the method further comprising storing the second electrical signal in a memory, wherein modifying the operation of the cardiac signal sensing module comprises stopping storage of the second electrical signal in the memory.

6. The method of claim 4, wherein modifying the operation of the cardiac signal sensing module comprises changing a frequency with which the cardiac signal sensing module senses the electrical activity of the heart.

7. The method of claim 3, wherein the threshold range of values comprises a threshold range of values relative to a reference value.

8. The method of claim 7, wherein the perfusion value comprises an oxygen variation index and the reference value is based on a trend of the oxygen variation index over time.

9. The method of claim 7, further comprising determining the reference value, wherein determining the reference value comprises:
   determining a plurality of perfusion values during a predetermined period of time; and
   determining the reference value based on the plurality of perfusion values.

10. The method of claim 9, wherein determining the reference value based on the plurality of perfusion values comprises determining a mean perfusion value of the plurality of perfusion values, wherein the reference value comprises the mean perfusion value.

11. The method of claim 9, wherein determining the reference value based on the plurality of perfusion values comprises:
- determining a mean perfusion value of the plurality of perfusion values;
- determining a deviation of each perfusion value of the plurality of perfusion values from the mean perfusion value;
- determining a mean deviation value based on the deviation of each perfusion value of the plurality of perfusion values from the mean perfusion value; and
- wherein the reference value comprises the mean perfusion value and the threshold range comprises the mean deviation value.

12. The method of claim 3, wherein modifying the operation of the cardiac signal sensing module comprises deactivating the cardiac signal sensing module if the perfusion value is within the threshold range of values.

13. The method of claim 1, wherein the perfusion value comprises at least one of an oxygen variation index or an amplitude of the electrical signal.

14. A system comprising:
- an optical perfusion sensing module that is configured to generate a first electrical signal indicative of a blood oxygen saturation level of a patient;
- a cardiac signal sensing module that is configured to generate a second electrical signal indicative of electrical activity of a heart of the patient; and
- a processor that is configured to receive the first electrical signal from the optical perfusion sensing module, and modify an operation of the cardiac signal sensing module based on a perfusion value that is based on the first electrical signal from the optical perfusion sensing module, wherein the processor is configured to modify the operation of the cardiac signal sensing module by at least activating the cardiac signal sensing module to sense electrical activity of the heart.

15. The system of claim 14, wherein the processor is configured to determine whether the perfusion value based on the first electrical signal is within a threshold range of values, and activate the cardiac signal sensing module to sense electrical activity of the heart if the perfusion value is not within the threshold range of values.

16. The system of claim 15, further comprising a memory, wherein the processor is configured to store at least one of the first electrical signal or the perfusion value in the memory, and if the perfusion value is not within the threshold range of values, the processor stores the second electrical signal within the memory.

17. The system of claim 15, wherein the processor is configured to modify the operation of the cardiac signal sensing module if the perfusion value is within the threshold range of values.

18. The system of claim 17, further comprising a memory, wherein the processor is configured to store the second signal and at least one of the first electrical signal or the perfusion value in the memory, and wherein the processor is configured to modify the operation of the cardiac signal sensing module by at least stopping storage of the second electrical signal in the memory.

19. The system of claim 17, wherein the processor is configured to modify the operation of the cardiac signal sensing module by at least changing a frequency with which the cardiac signal sensing module senses the electrical activity of the heart.

20. The system of claim 15, wherein the threshold range of values comprises a threshold range relative to a reference value.

21. The system of claim 20, wherein the processor is configured to determine the reference value by at least:
- determining a plurality of perfusion values during a predetermined period of time; and
- determining the reference value based on the plurality of perfusion values.

22. The system of claim 21, wherein each perfusion value of the plurality of perfusion values comprises an oxygen variation index, and the reference value is based on a trend of the oxygen variation index over time.

23. The system of claim 22, wherein the processor is configured to deactivate the cardiac signal sensing module if the perfusion value is within the threshold range of values.

24. The system of claim 14, wherein the perfusion value comprises at least one of an oxygen variation index or an amplitude of the first electrical signal.

25. A system comprising:
- means for receiving an electrical signal from an optical perfusion sensor, wherein the electrical signal is indicative of blood oxygen saturation of tissue of a patient; and
- means for modifying an operation of a cardiac signal sensing module that senses electrical activity of a heart of the patient based on a perfusion value that is based on the electrical signal, wherein the means for modifying modifies an operation of the cardiac signal sensing module by at least activating the cardiac signal sensing module to sense electrical activity of the heart.

26. A computer-readable medium comprising instructions that cause a programmable processor to:
- receive an electrical signal from an optical perfusion sensor, wherein the electrical signal is indicative of blood oxygen saturation of tissue of a patient; and
- modify an operation of a cardiac signal sensing module that senses electrical activity of a heart of the patient based on a perfusion value that is based on the electrical signal, wherein the instructions cause the programmable processor to modify the operation of the cardiac signal sensing module by at least activating the cardiac signal sensing module to sense electrical activity of the heart.

* * * * *